(12) United States Patent
Bullerdiek et al.

(10) Patent No.: US 8,828,656 B2
(45) Date of Patent: Sep. 9, 2014

(54) MICRORNA-BASED METHODS AND COMPOSITIONS FOR THE DIAGNOSIS, PROGNOSIS AND TREATMENT OF TUMOR INVOLVING CHROMOSOMAL REARRANGEMENTS

(75) Inventors: Joern Bullerdiek, Bremen (DE); Volkhard Rippe, Emtinghausen (DE)

(73) Assignee: University of Bremen (DE)

( * ) Notice: Subject to any disclaimer, the term of this patent is extended or adjusted under 35 U.S.C. 154(b) by 45 days.

(21) Appl. No.: 13/393,122

(22) PCT Filed: Aug. 31, 2010

(86) PCT No.: PCT/EP2010/005349
§ 371 (c)(1),
(2), (4) Date: Jul. 31, 2012

(87) PCT Pub. No.: WO2011/023414
PCT Pub. Date: Mar. 3, 2011

(65) Prior Publication Data
US 2012/0295949 A1 Nov. 22, 2012

(30) Foreign Application Priority Data
Aug. 31, 2009 (EP) .................................... 09011141

(51) Int. Cl.
*C12Q 1/68* (2006.01)
*C07H 21/02* (2006.01)
*C07H 21/04* (2006.01)

(52) U.S. Cl.
USPC ............................. 435/6; 536/23.1; 536/24.5

(58) Field of Classification Search
None
See application file for complete search history.

(56) References Cited

U.S. PATENT DOCUMENTS

2010/0131432 A1* 5/2010 Kennedy et al. .............. 705/500

FOREIGN PATENT DOCUMENTS

WO WO 2008/002672 1/2008

OTHER PUBLICATIONS

Pfister, et al. "Novel genomic amplification targeting the microRNA cluster at 19q13.42 in a pediatric embryonal tumor with abundant neuropll and true rosettes" ACTA Neuropathologica, vol. 117, No. 4, Apr. 2009, pp. 457-464.
Huang, et al. "The microRNAs miR-373 and miR-520c promote tumour invasion and metastasis" Nature Cell Biology, vol. 10, No. 2, Feb. 2008, p. 202
Voorhoeve, et al, "A genetric screen implicates miRNA-372 and miRNA-373 as oncogenes in testicular germ cell tumors" Cell, vol. 124, No. 6, Mar. 2006, pp. 1169-1181.
Laurent, et al. "Comprehensive microRNA profiling reveals a unique human embryonic stem cell signature dominated by a single seed sequence" Stem Cells, vol. 26, No. 6, Jun. 2008, pp. 1506-1516.
Weber, et al. "A Limited set of human MicroRNA is deregulated in follicular thyroid carcinoma" Journal of Clinical Endocrinology and Metabolism, vol. 91, No. 9, Sep. 2006, pp. 3584-3591.
Nikiforova, et al. "MicroRNA expression profiles in thyroid tumors" Endocrine Pathology, vol. 20, No. 2, Jul. 2009, pp. 85-91.
Calin, et al., "Chromosomal rearrangements and microRNAs: a new cancer link with clinical implications" Journal of Clinical Investigation, vol. 117, No. 8, Aug. 2007, pp. 2059-2066.
Drieschner, et al. "Evidence for a 3p25 breakpoint hot spot region in thyroid tumors of follicular origin" Thyroid: Official Journal of the American Thyroid Association, vol. 16, No. 11, Nov. 2006, pp. 1091-1096.
Rippe, et al. "The two stem cell microRNA gene clusters C19MC and miR-371-3 are activated by specific chromosomal rearrangements in a subgroup of thyroid adenomas" PLOS One, vol. 5, No. 3 E9465, Mar. 3, 2010, pp. 1-11.

* cited by examiner

*Primary Examiner* — Amy Bowman
(74) *Attorney, Agent, or Firm* — Sheridan Ross P.C.

(57) ABSTRACT

Provided are novel methods and compositions for the diagnosis, prognosis and treatment of tumor involving a chromosomal rearrangement, in particular a tumor or neoplasia of the thyroid gland. In addition, methods of identifying anti-tumor agents are described.

15 Claims, 14 Drawing Sheets

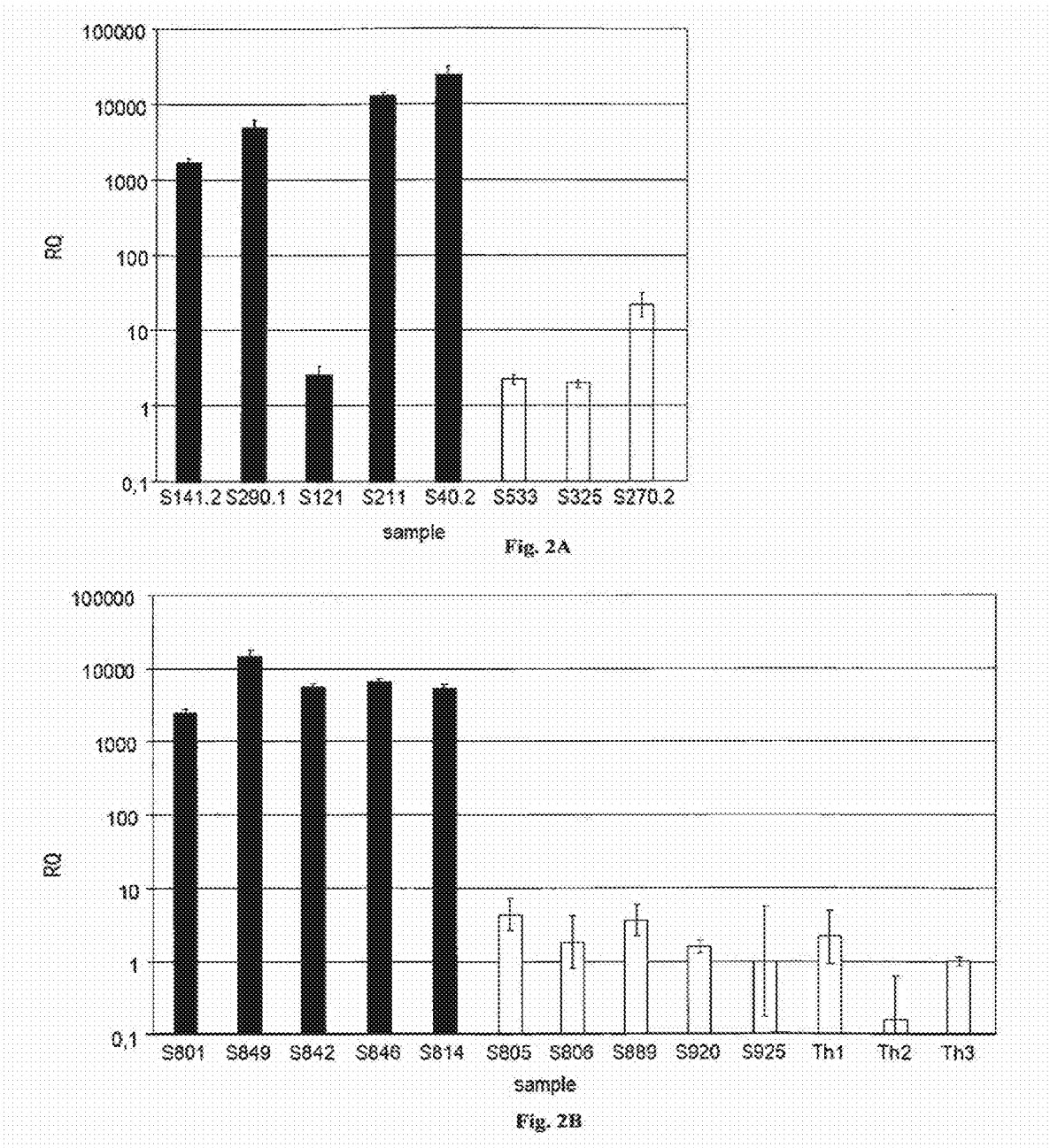

US 8,828,656 B2

MICRORNA-BASED METHODS AND COMPOSITIONS FOR THE DIAGNOSIS, PROGNOSIS AND TREATMENT OF TUMOR INVOLVING CHROMOSOMAL REARRANGEMENTS

CROSS-REFERENCE TO RELATED APPLICATION

This application is a National Stage of PCT/EP2010/005349, filed Aug. 31, 2010 which claims priority to European Application No. 09011141.0, filed Aug. 31, 2009, the disclosures of which are incorporated herein by reference in their entirety.

FIELD OF THE INVENTION

The present invention relates generally to the field of molecular biology. More particularly, it concerns methods and compositions involving microRNA (miRNAs or miRs) molecules. Methods and compositions for isolating, labeling, preparing miRNAs for analysis or as a tool for analysis are described, such as miRNA arrays. In addition, there are applications for miRNAs in diagnostics, therapeutics, and prognostics. More specifically, the present invention relates to the use of miRs, in particular those belonging to a miR cluster located in proximity to a chromosomal breakpoint region as a diagnostic and therapeutic target in the treatment of tumors involving chromosomal rearrangements.

The instant application contains a Sequence Listing which has been submitted in ASCII format via EFS-Web and is hereby incorporated by reference in its entirety. Said ASCII copy, created on Feb. 28, 2012, is named 0051_0058_US1_Sequence_Listing.txt and is 39641 bytes in size.

BACKGROUND OF THE INVENTION

The development of tumor often involves a chromosomal rearrangement such as translocation resulting in altered gene regulation and expression. For example, thyroid adenoma is a tumor showing clonal chromosomal abnormalities with trisomy 7 and chromosomal rearrangements. Thyroid adenomas are highly frequent human tumors that can be distinguished from their malignant counterparts, i.e. follicular carcinomas by an encapsulated growth and a lack of invasiveness, respectively. Even in iodine sufficient areas thyroid adenomas occur in 4-7% of adults and in iodine deficient areas this number can rise to about 50%. The pathogenesis of these frequent benign tumors is only poorly understood but clonal chromosomal aberrations can be observed in roughly 40% of the nodules and are likely to pinpoint genomic regions and genes relevant for the development of the disease (DeLellis, Pathology and genetics of tumours of endocrine organs, editorial and consensus conference in Lyon, France, Apr. 23-26, 2003, 320 S. IARC Press, Lyon, 2004). Roughly 20% of the tumors show clonal chromosomal abnormalities with trisomy 7 (Bartnitzke et al., Cancer Genet. Cytogenet. 39 (1989), 65-68) and about 20% of the tumors with clonal cytogenetic aberrations show abnormalities involving chromosomal band 19q13 (Belge et al., Cancer Genet. Cytogenet. 101 (1998), 42-48). Given the extremely high prevalence of thyroid adenomas in Europe and the U.S. alone four to five million people can be estimated to be affected by this genomic alteration in their thyroid. The 19q13 breakpoint has been assigned to a segment of 150 kb by positional cloning and possible target genes in that cluster region have been investigated in some detail (Beige et al., Cytogenet. Cell Genet. 93, (2001), 48-51; Rippe, et al., Genes Chromosomes Cancer 26 (1999), 229-236). However, the long arm of chromosome 19 shows an extraordinary high gene density compared to other regions of the human genome, and so far only protein-encoding genes have been considered as targets of these highly frequent structural chromosome abnormalities.

In spite of considerable research into therapies for tumor involving chromosomal aberrations, this type of tumor and in particular thyroid adenoma remains difficult to diagnose and treat effectively, and indicates that improvements are needed in the diagnosis, treatment and prevention of the disease.

SUMMARY OF THE INVENTION

The present invention is based, in part, on the identification of a thyroid adenoma-specific signature of two microRNA (miRNA) gene clusters, i.e. C19MC and miR-371-3 that are located in close proximity to the breakpoint region of a chromosomal rearrangement and become consistently activated relative to normal control cells.

Accordingly, the present invention encompasses methods of diagnosing whether a subject has, or is at risk for developing a tumor preferably involving a chromosomal rearrangement comprising measuring the level of at least one microRNA (miR) in a test sample from the subject. An alteration in the level of the miR in the test sample, relative to the level of a corresponding miR in a control sample, is indicative of the subject either having, or being at risk for developing said tumor.

In a particular aspect, there is provided herein a method of diagnosing whether a subject has, or is at risk for developing a tumor or neoplasia of the thyroid gland, said method comprising measuring the level of at least one microRNA (miR) in a test sample from the subject. An alteration, in particular increase in the level of the miR in the test sample, relative to the level of a corresponding miR in a control sample, is indicative of the subject either having, or being at risk for developing a tumor or neoplasia of the thyroid gland.

In another particular aspect, there is provided herein a method that includes identifying a correlation between miR expression and a tumor preferably involving a chromosomal rearrangement, in particular chromosomal translocation or a predisposition for said tumor, comprising: (a) labeling the miR isolated from a sample from a subject having or suspected of having a disease or condition; (b) hybridizing the miR to an miR array; (c) determining miR hybridization to the array; and (d) identifying miR differentially expressed in a sample representative of the disease or condition compared to a reference.

In a particular aspect, there is provided herein a method that includes identifying a correlation between miR expression and a tumor preferably involving a chromosomal rearrangement on chromosome 19, in particular chromosomal band 19q13, comprising measuring the level of at least one microRNA (miR) in a test sample from the subject. An alteration, in particular increase in the level of the miR in the test sample, relative to the level of a corresponding miR in a control sample, is indicative of the subject either having, or being at risk for developing said tumor.

Typically, the methods of the present invention comprise measuring the level of at least one miR in a test sample, wherein the miR is or belongs to a miR cluster located in proximity to a breakpoint region associated with the chromosomal rearrangement, in particular chromosomal translocation.

In a particular aspect, there is provided herein a method where identifying miR differentially expressed comprises generating an miR profile for the sample and evaluating the miR profile to determine whether miR in the sample are differentially expressed compared to a normal sample. In certain embodiments, the miR profile is selected from one or more of the miRs of the C19MC cluster and/or miR-371-3 cluster such as shown in Table 3. Preferably, the miR profile is selected from one or more of the miRs of the miR-371-3 cluster.

In a particular aspect, the tumor preferably involving a chromosomal rearrangement is one or more of a tumor or neoplasia of the thyroid gland, in particular thyroid adenoma. In a particular aspect, the miR profile is selected from one or more of the miRs shown in Table 3, whereby thyroid adenoma cells are distinguished from normal cells.

In a particular embodiment, the miR profile involves at least one miR selected from the group consisting of miR-512-5p, miR-517a, miR-519a, miR-520c, miR-371-3p, miR-372 and miR-373, wherein a difference in expression of one or more of the miRNA compared to a normal sample is indicative of thyroid adenoma.

In a particular aspect, there is provided herein a method wherein an increase in expression of hsa-mir-371; hsa-miR-371-3p; hsa-miR-371-5p; hsa-miR-372; hsa-miR-373; hsa-miR-373*; hsa-mir-512-1; hsa-miR-512-5p; hsa-miR-512-3p; hsa-mir-512-2; hsa-miR-512-5p; hsa-miR-512-3p; hsa-mir-515-1; hsa-miR-515-5p; hsa-miR-515-3p; hsa-mir-515-2; hsa-miR-515-5p; hsa-miR-515-3p; hsa-mir-516a-1; hsa-miR-516a-5p; hsa-miR-516a-3p; hsa-mir-516a-2; hsa-miR-516a-5p; hsa-miR-516a-3p; hsa-mir-516b-1; hsa-miR-516b; hsa-miR-516b*; hsa-mir-518b; hsa-miR-517a; hsa-miR-517*; hsa-miR-517b; hsa-miR-517*; hsa-mir-517c; hsa-miR-517*; hsa-mir-518a-1; hsa-miR-518a-5p; hsa-miR-518a-3p; hsa-mir-518a-2; hsa-miR-518a-5p; hsa-miR-518a-3p; hsa-miR-518b; hsa-miR-518c; hsa-miR-518c*; hsa-mir-518d; hsa-miR-518d-5p; hsa-miR-518d-3p; hsa-miR-518e; hsa-miR-518e*; hsa-mir-518f; hsa-miR-518f*; hsa-mir-519a-1; hsa-miR-519a; hsa-miR-519a*; hsa-mir-519a-2; hsa-mir-519b; hsa-miR-519b-5p; hsa-miR-519b-3p; hsa-mir-519c; hsa-miR-519c-5p; hsa-miR-519c-3p; hsa-miR-519d; hsa-mir-519e; hsa-miR-519e; hsa-miR-519e*; hsa-mir-520a; hsa-miR-520a-5p; hsa-miR-520a-3p; hsa-miR-520b; hsa-mir-520c; hsa-miR-520c-5p; hsa-miR-520c-3p; hsa-mir-520d; hsa-miR-520d-5p; hsa-miR-520d-3p; hsa-mir-520e; hsa-miR-520f; hsa-miR-520g; hsa-miR-520h; hsa-mir-521-1; hsa-mir-521-2; hsa-miR-521; hsa-mir-522; hsa-miR-522*; hsa-mir-523; hsa-miR-523*; hsa-mir-524; hsa-miR-524-5p; hsa-miR-524-3p; hsa-miR-525; hsa-miR-525-5p; hsa-miR-525-3p; hsa-mir-526a-1; hsa-miR-526a; hsa-mir-526a-2; hsa-mir-526b; hsa-miR-526b*; and/or hsa-miR-527; (for details see Table 1), as compared to a normal sample, is indicative of thyroid adenoma.

In some embodiments of the method of the present invention the tumor preferably involving a chromosomal rearrangement is associated with one or more prognostic markers in a subject. For example, in case of thyroid adenoma the prognostic marker is trisomy 7. In addition, molecular diagnostic markers, i.e. nucleic acid sequences and proteins of tumors and neoplasias of the thyroid gland are described in international applications WO2003/093310, WO2002/083727 and WO2001/027265, the disclosure content of which is incorporated herein by reference.

In a particular aspect, there is provided herein a method of inhibiting proliferation of a cell of a tumor preferably involving a chromosomal rearrangement comprising:
(i) introducing into the cell one or more agents which inhibit expression or activity of one or more miRs which expression is induced or increased in the tumor cell having a chromosomal rearrangement, relative to a control cell; and
(ii) maintaining the cell under conditions in which the one or more agents inhibits expression or activity of the miR, thereby inhibiting proliferation of the tumor cell.

In a particular embodiment, the cell is a human cell.

In a particular aspect, there is provided herein a method where the expression of miR-371-3p, miR-372 and miR-373 are up-regulated, and have as common putative target the tumor suppressor LATS2 or other genes involved in the control of cell proliferation, that are down-modulated in a tumor preferably involving a chromosomal rearrangement such as in thyroid tumor, i.e. thyroid adenoma.

In a particular aspect, there is provided herein a method for modulating levels of one or more miR of the C19MC cluster and/or at least one miR of the miR-371-3 cluster in a cell of a tumor preferably involving a chromosomal rearrangement compared with normal tissues, comprising administering an effective amount of an agent that reduces or inhibits the expression of the pumilio homolog 1 (PUM1) gene, which is in some instances is responsible for their over-expression; see Example 4.

The level of the at least one miR can be measured using a variety of techniques that are well known to those of skill in the art. In one embodiment, the level of the at least one miR is measured using Northern blot analysis. In another embodiment, the level of the at least one miR in the test sample is greater than the level of the corresponding miR in the control sample.

The invention also provides methods of diagnosing a tumor associated with one or more prognostic markers in a subject, comprising measuring the level of at least one miR in a tumor sample from the subject, wherein an alteration, in particular increase in the level of the at least one miR in the test sample, relative to the level of a corresponding miR in a control sample, is indicative of the subject having a tumor associated with the one or more prognostic markers. In one embodiment, the level of the at least one miR is measured by reverse transcribing RNA from a test sample obtained from the subject to provide a set of target oligodeoxynucleotides; hybridizing the target oligodeoxynucleotides to a microarray comprising miR-specific probe oligonucleotides to provide a hybridization profile for the test sample; and, comparing the test sample hybridization profile to a hybridization profile generated from a control sample. An alteration in the signal of at least one miR is indicative of the subject either having, or being at risk for developing, such tumor. In one embodiment, the prognostic markers comprise adverse prognostic markers such as clonal cytogenetic aberrations, for example clonal chromosomal abnormalities with trisomy 7 and structural alterations, in particular involving chromosomal band 19q13.

The invention also encompasses methods of treating tumor in a subject, wherein the signal of at least one miR, relative to the signal generated from the control sample, is de-regulated (e.g., up-regulated).

The invention also encompasses methods of diagnosing whether a subject has, or is at risk for developing, a tumor associated with one or more adverse prognostic markers in a subject, by reverse transcribing RNA from a test sample obtained from the subject to provide a set of target oligodeoxynucleotides; hybridizing the target oligodeoxynucleotides to a microarray comprising miR-specific probe oligonucleotides to provide a hybridization profile for the test sample; and, comparing the test sample hybridization profile to a hybridization profile generated from a control sample. An alteration, in particular increase in the signal is indicative of the subject either having, or being at risk for developing, the tumor.

The invention also encompasses methods of treating tumor in a subject who has a tumor in which at least one miR is up-regulated in the tumor cells of the subject relative to control cells. When the at least one miR is up-regulated in the tumor cells, the method comprises administering to the subject an effective amount of at least one compound for inhibiting expression of the at least one miR, such that proliferation of tumor cells in the subject is inhibited.

In related embodiments, the invention provides methods of treating tumor in a subject, comprising: determining the amount of at least one miR in tumor cells, relative to control cells; and altering the amount of miR expressed in the tumor cells by administering to the subject an effective amount of at least one isolated miR, if the amount of the miR expressed in the tumor cells is greater than the amount of the miR expressed in control cells, such that proliferation of tumor cells in the subject is inhibited.

The invention further provides pharmaceutical compositions for treating tumor, comprising at least one miR expression inhibitor compound and a pharmaceutically acceptable carrier. More particularly, the present invention relates to a pharmaceutical composition for treating a subject suffering from a tumor preferably involving a chromosomal rearrangement, said composition comprising a compound capable of inhibiting expression of at least one miR which belongs to a miR cluster located in proximity to a breakpoint region of the chromosomal rearrangement or decreasing the amount or level of activity of the miR; and optionally a pharmaceutically acceptable carrier. Usually, the subject to be treated has been diagnosed in accordance with a method of the present invention to suffer from the tumor.

In other embodiments, the present invention provides of identifying an anti-tumor agent for a tumor, comprising providing a test agent to a cell and measuring the level of at least one miR associated with increased expression levels in tumor cells having a chromosomal rearrangement, wherein a decrease in the level of the miR in the cell, relative to a suitable control cell, is indicative of the test agent being an anti-tumor agent.

In a further embodiment, the present invention relates to a kit useful in a method of the present invention for diagnosing whether a subject has, or is at risk for developing, a tumor; for a method of the present invention including identifying a correlation between miR expression and a tumor preferably involving a chromosomal rearrangement; or for a method of the present invention for identifying an anti-tumor agent as described herein, said kit comprising one or more reagents for detecting one or more miRs.

In a specific aspect, as disclosed herein, at least one miR is selected from the C19MC cluster and/or the miR-371-3 cluster. In a particular embodiment the miR is selected from the group consisting of miR-512-5p, miR-517a, miR-519a, miR-520c, miR-371-3p, miR-372, and miR-373.

In a specific aspect, the tumor preferably involving a chromosomal rearrangement, i.e. chromosomal translocation and in particular a balanced translocation involving 19q13.4 is as human neoplasia, more specifically a human epithelial tumor such as thyroid adenoma, a mesenchymal tumor or a lymphoma.

In a specific aspect, there is also provided herein the identification of miRNAs whose expression is correlated with specific thyroid tumors, i.e. thyroid adenoma biopathologic features, such as histotype, encapsulated growth and a lack of invasiveness, and prevalence in iodine sufficient areas.

In a preferred embodiment, the methods of the present invention comprise the simultaneous analysis and targeting, respectively, of miR clusters, in particular the C19MC cluster and/or the miR-371-3 cluster, and more preferably one or several of the microRNAs encoded by any one of or both of said C19MC and miR-371-3 cluster.

In another particular aspect, there is also disclosed herein a method for altering the expression of these miRs by controlling the mechanism responsible for their activation and over-expression, for example by down-regulating the PUM1 promoter or otherwise interfering with the expression, stability, degradation, etc of fusion transcripts between the proximal part of PUM1 exon/intron sequences and sequences from chromosome 19, in particular of the C19MC cluster and/or the miR-371-3 cluster. Compositions and methods for modulating the expression of PUM1, particularly oligonucleotide compounds, which hybridize with nucleic acid molecules encoding PUM1 are known to the person skilled in the art and described in, e.g., US patent application US 2005/0261217A1, the disclosure content of which is incorporated herein by reference Various objects and advantages of this invention will become apparent to those skilled in the art from the following detailed description of the preferred embodiments and Examples, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) may be provided by the European Patent Office or United States Patent and Trademark Office upon request and payment of the necessary fee.

miR-371-3 expression in thyroid cell lines, five cell lines derived from adenomas with 19q13.4 rearrangements (black bars (miR-371-3p), large squared bars (miR-372) and small squared bars (miR-373)) and three cell lines derived from thyroid adenomas with other structural rearrangements (black dotted bars (miR-371-3p), diagonally striped bars (miR-372) and horizontally striped bars (miR-373)) (for case numbers refer to Table 2). High variation of s.d. is due to very high Ct values.

Figure 1:
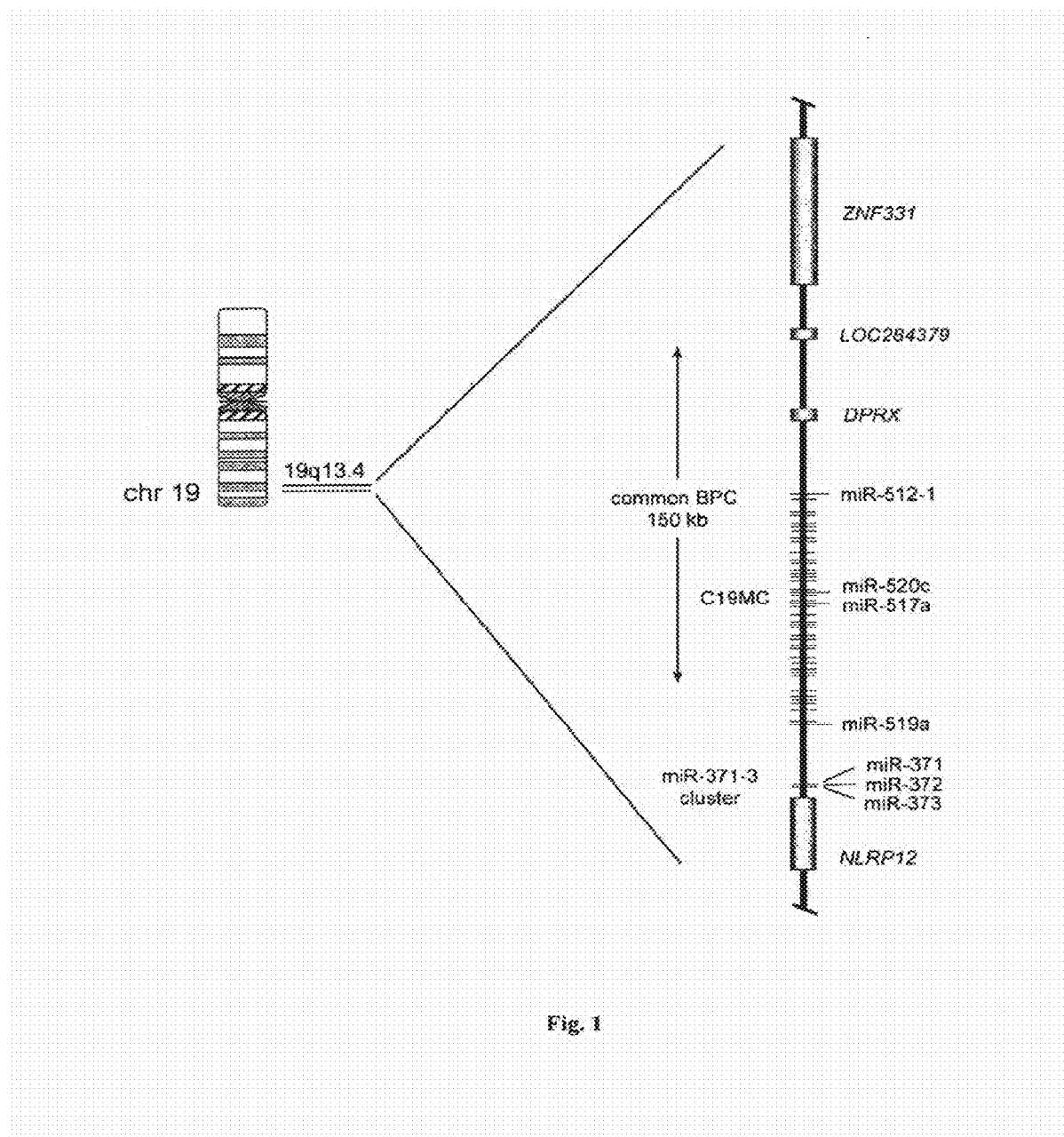
FIG. 1: Scheme of the chromosomal region 19q13.4 with the two miRNA clusters C19MC and miR-371-3. The common breakpoint cluster (BPC) of benign thyroid tumors of about 150 kb is indicated by a vertical arrow. miR-512-1 (pre-miR) is coding for mature-miR-512-5p, miR-371 (pre-miR) is coding for mature-miR371-3p. Gene symbols refer to the following protein coding genes: ZNF331=zinc finger protein 331, DPRX=divergent-paired related homeobox, NLRP12=NLR family, pyrin domain containing 12.
Figure 2C:
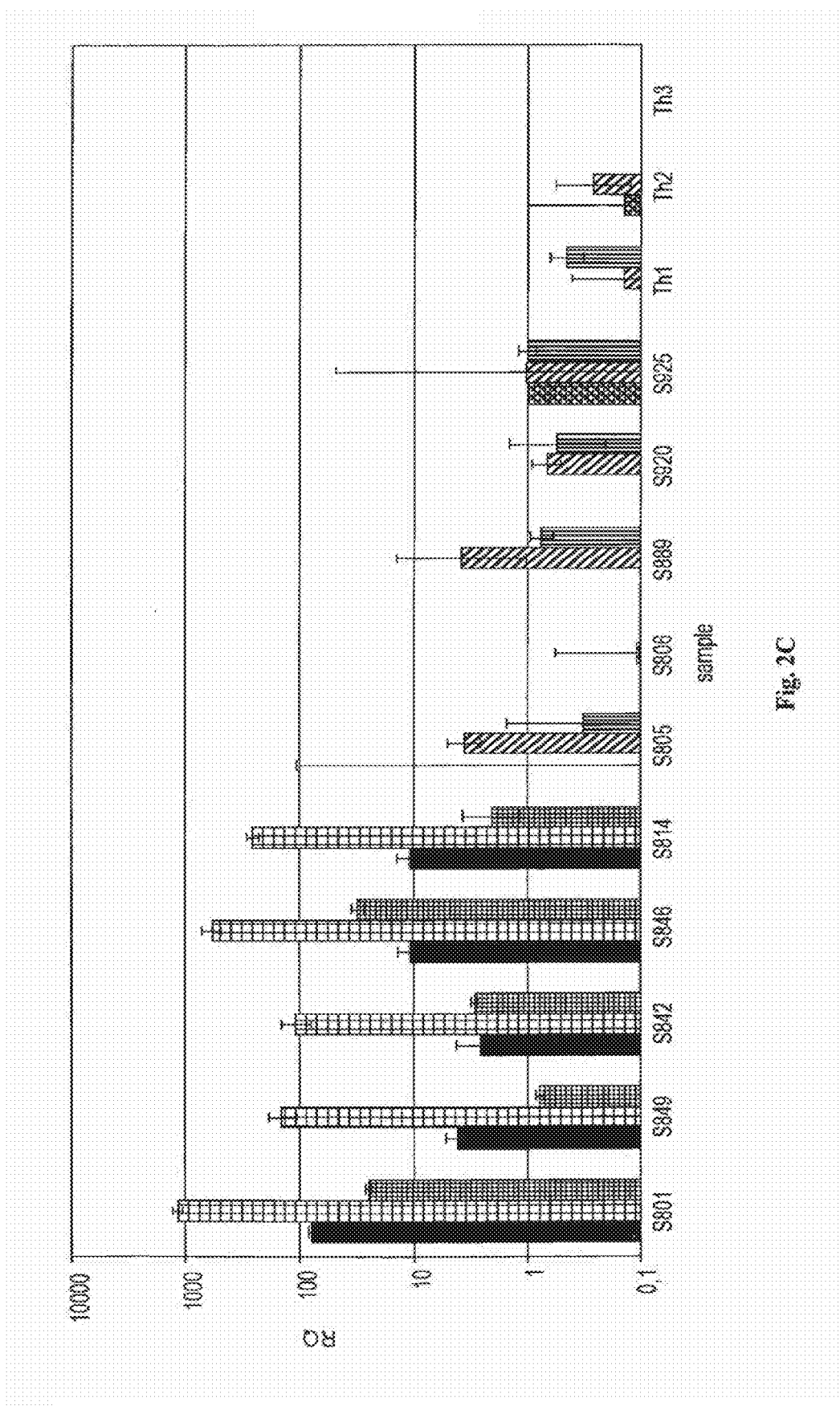
FIG. 2: Expression of miR-520c, miR-371-3p, miR-372 and miR-373 in cell lines and primary tumors. Relative expression of miRNAs was determined by real-time PCR (mean s.d. from three independent experiments). Values of miRNA were normalized to RNU6B (RNA, U6 small nuclear 2) (A) miR-520c expression in thyroid cell lines, five cell lines derived from adenomas with 19q13.4 rearrangements (S141.2, S290.1, S121, S211, S40.2) (black bars) and three cell lines derived from thyroid adenomas with other structural rearrangements (S533, S325, S270.2) (white bars). (B) miR-520c expression in three samples of non-neoplastic thyroid tissues (Th1, Th2, Th3) (white bars), five adenomas with 19q13.4 rearrangement (S801, S849, S842, S846, S814) (black bars) and five adenomas without cytogenetically detectable aberrations (S805, S806, S889, S920, S925) (white bars). (C) miR-371-3 expression in three samples of non-neoplastic thyroid tissues (black dotted bars (miR-371-3p), diagonally striped bars (miR-372) and horizontally striped bars (miR-373)), five adenomas with 19q13.4 rearrangement (black bars (miR-371-3p), large squared bars (miR-372) and small squared bars (miR-373)) and five adenomas without cytogenetically detectable aberrations (black dotted bars, diagonally striped bars and horizontally striped bars bars) (for case numbers refer to Table 2). (D)
Figure 2D:
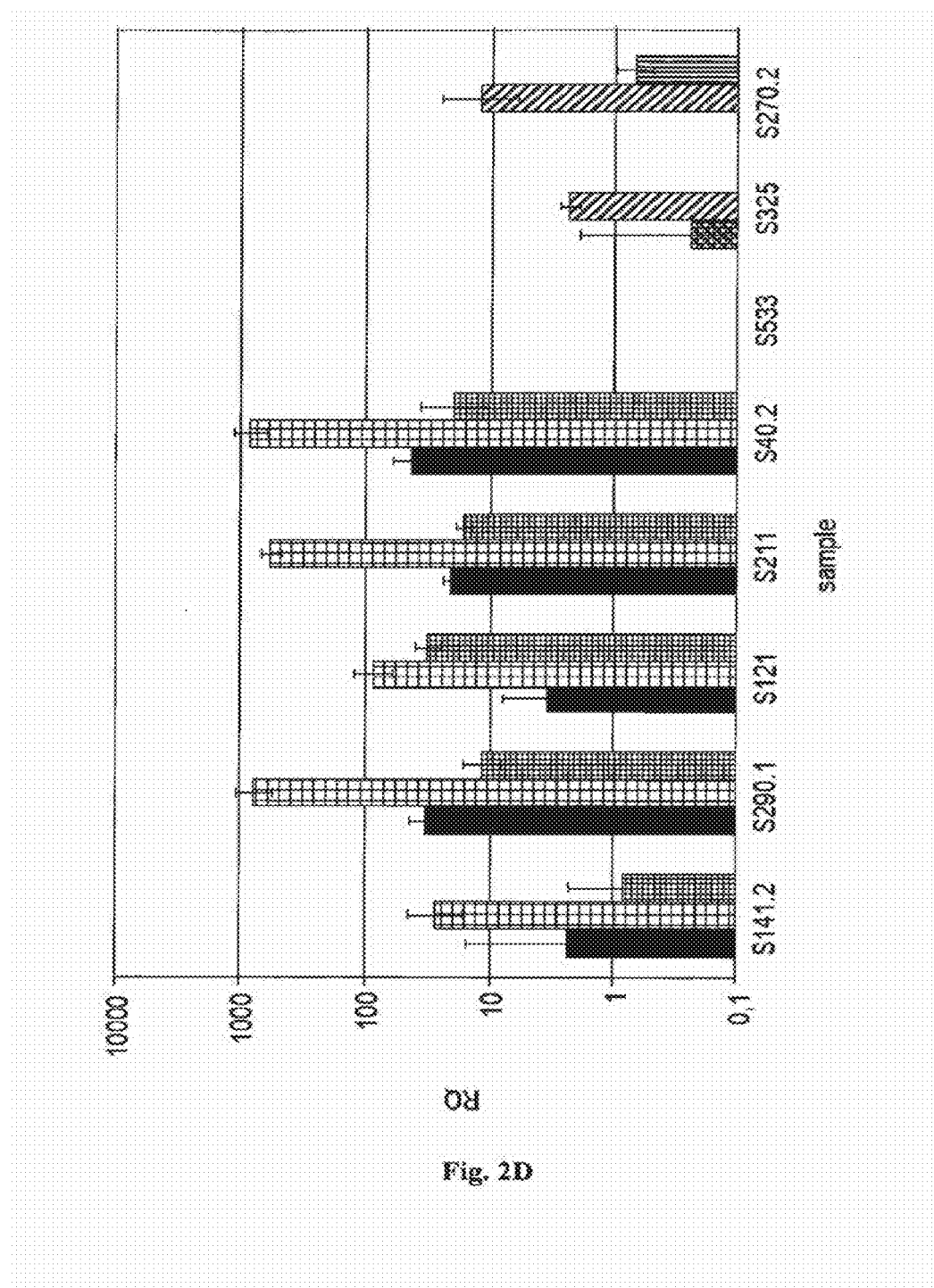
Figure 3:
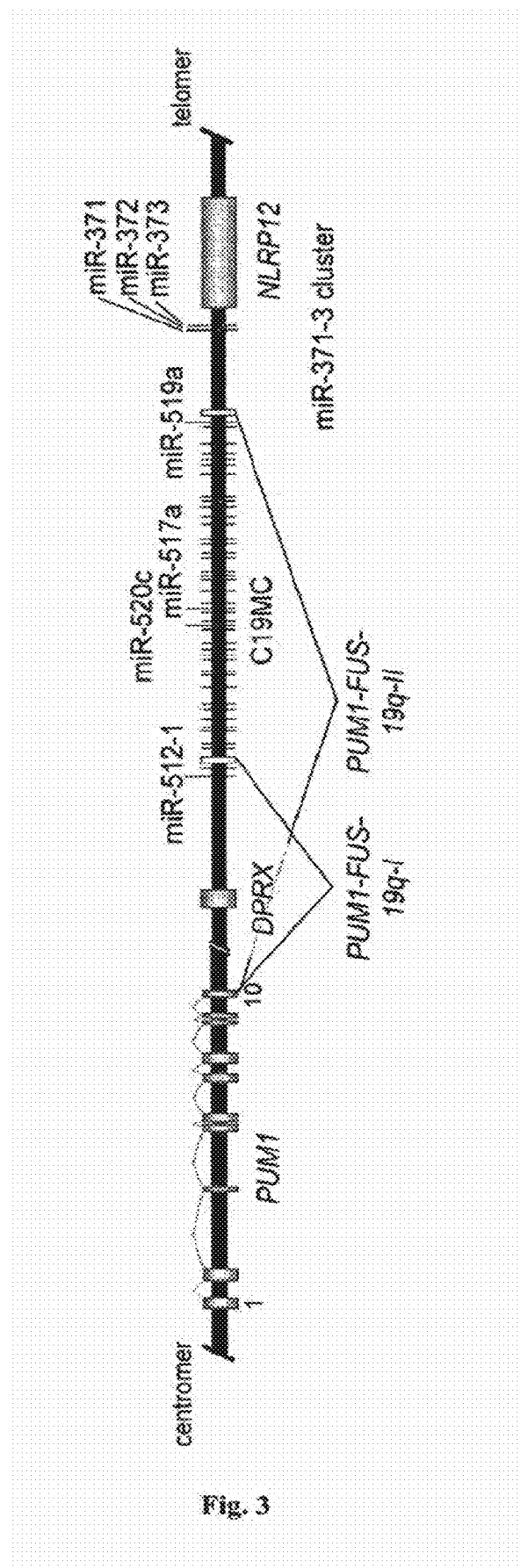

FIG. 3: Genomic organization of the fusion gene on the derivative chromosome 1 resulting from a translocation t(1;19)(p35.2;13.4) in cell line S40.2. Detailed schematic overview illustrating the origin of the fusion transcripts PUM1-FUS-19q-I (Genbank Accession number GQ334687) and PUM1-FUS-19q-II (Genbank Accession number GQ334688) identified in cell line S40.2. The genomic region of PUM1 in 1p35.2 fuses after exon 10 of PUM1 to the genomic region of C19MC in 19q13.4. Two vertical bars indicate 3'-sequences located after exon 1-10 of PUM1 in PUM1-FUS-19q-I and PUM1-FUS-19q-II, respectively, both originating from alternative splicing. The fusion transcripts were detected either by 3'-RACE-PCR (PUM1-FUS-19q-I) or RT-PCR (PUM1-FUS-19q-II) experiments. The quantified miRNAs have been highlighted by their names.

Figure 4:
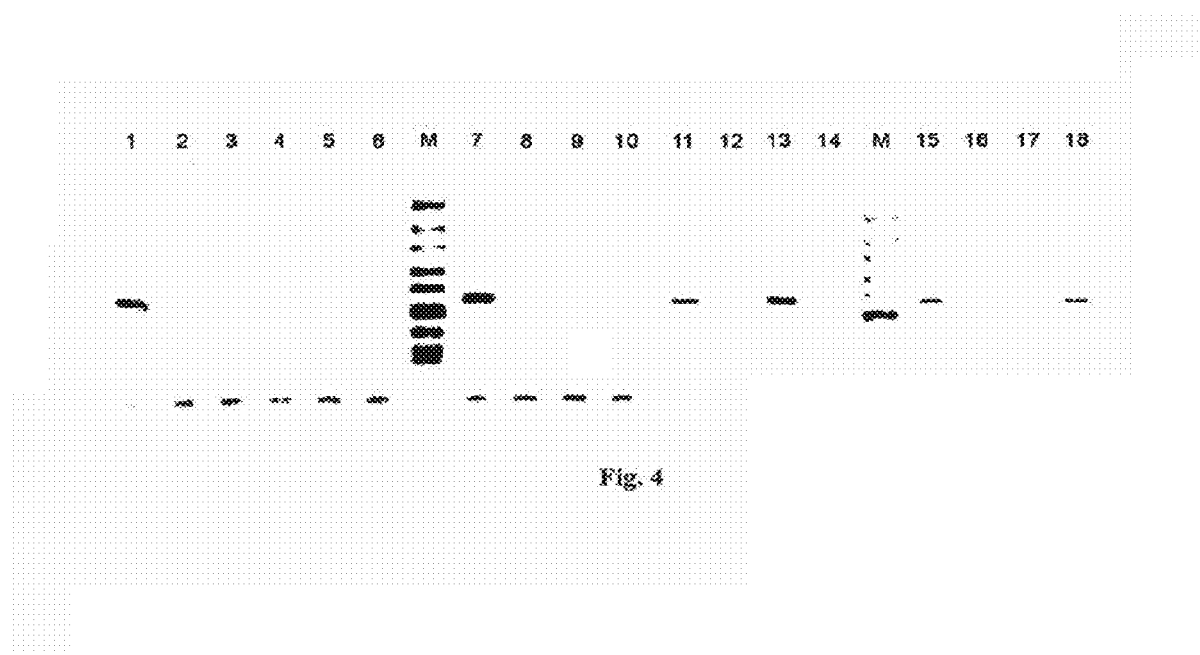

FIG. 4: Expression analysis of miR-517a by RT-PCR. PCR reactions were performed and then analyzed in 4% small DNA Agarose. The expected DNA-fragment has a size of 62 bp, Ultra low range Ladder (Fermentas) was used as Marker (M). Lane 1: S40.2, 2: S40.2 without reverse transcriptase (-RT), 3: S121, 4: S121-RT, 5: thyroid (normal), 6: thyroid-RT, 7: placenta, 8: placenta-RT, 9: S270.2, 10: S270.2-RT, 11: S290.1, 12: S290.1-RT, 13: S141.2, 14: S325, 15: S211, 16: S211-RT, 17: fetal RNA, 18: adult testis, 19: fetal RNA-RT, 20: S141.2-RT, 21: adult testis-RT, 22: S325-RT (for details of the cell lines and tumor samples see Table 1).

Figure 5:
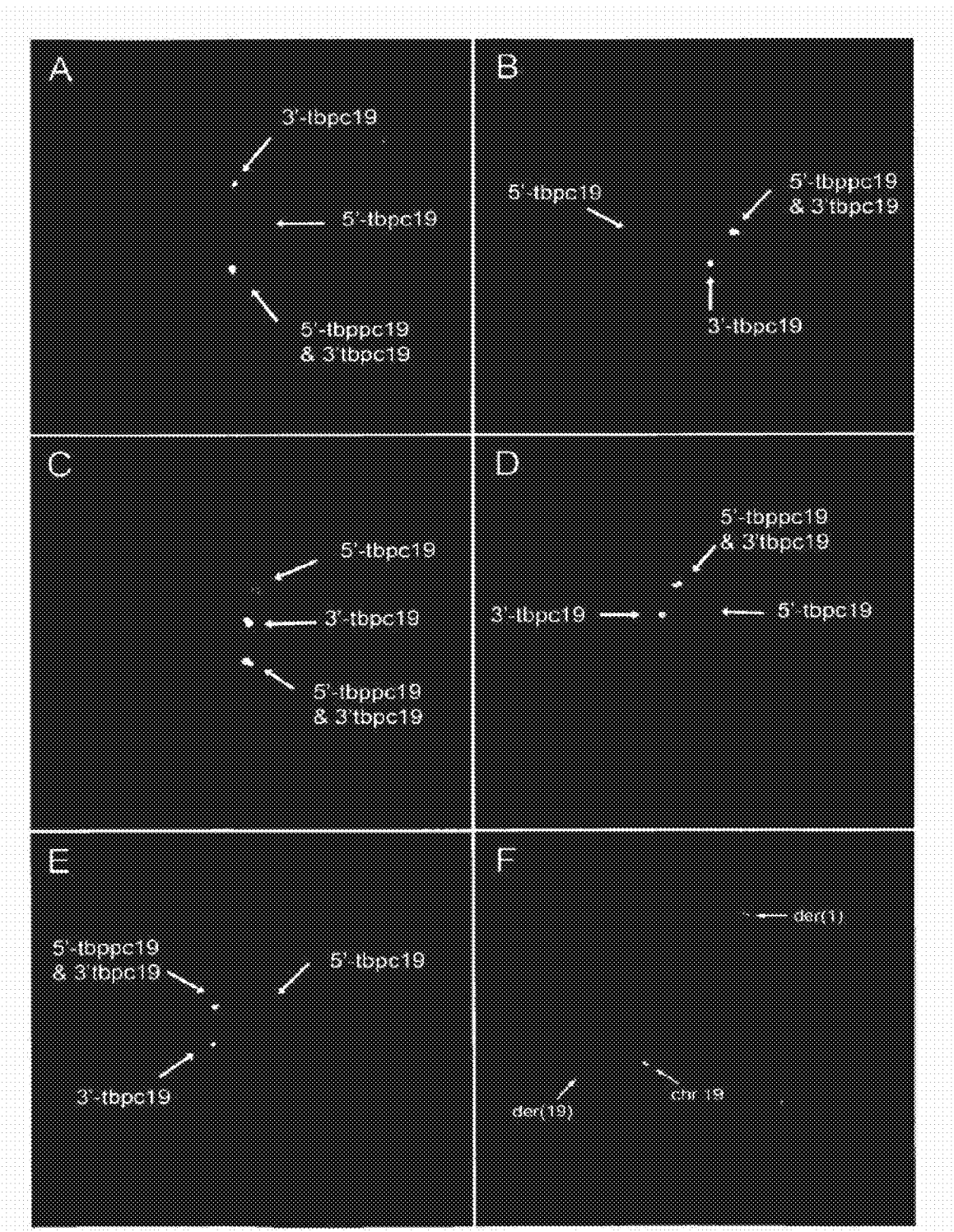

FIG. 5: Genomic organization of the fusion gene on the derivative chromosome 1 resulting from a translocation t(1;19)(p35.2;13.4) in cell line S40.2. Detailed schematic overview illustrating the origin of the fusion transcripts PUM1-FUS-19q-I (Genbank Accession number GQ334687) and PUM1-FUS-19q-II (Genbank Accession number GQ334688) identified in cell line S40.2. The genomic region of PUM1 in 1p35.2 fuses after exon 10 of PUM1 to the genomic region of C19MC in 19q13.4. Two vertical bars indicate 3'-sequences located after exon 1-10 of PUM1 in PUM1-FUS-19q-I and PUM1-FUS-19q-II, respectively, both originating from alternative splicing. The fusion transcripts were detected either by 3'-RACE-PCR (PUM1-FUS-19q-I) or RT-PCR (PUM1-FUS-19q-II) experiments. The quantified miRNAs have been highlighted by their names.

Figure 6:
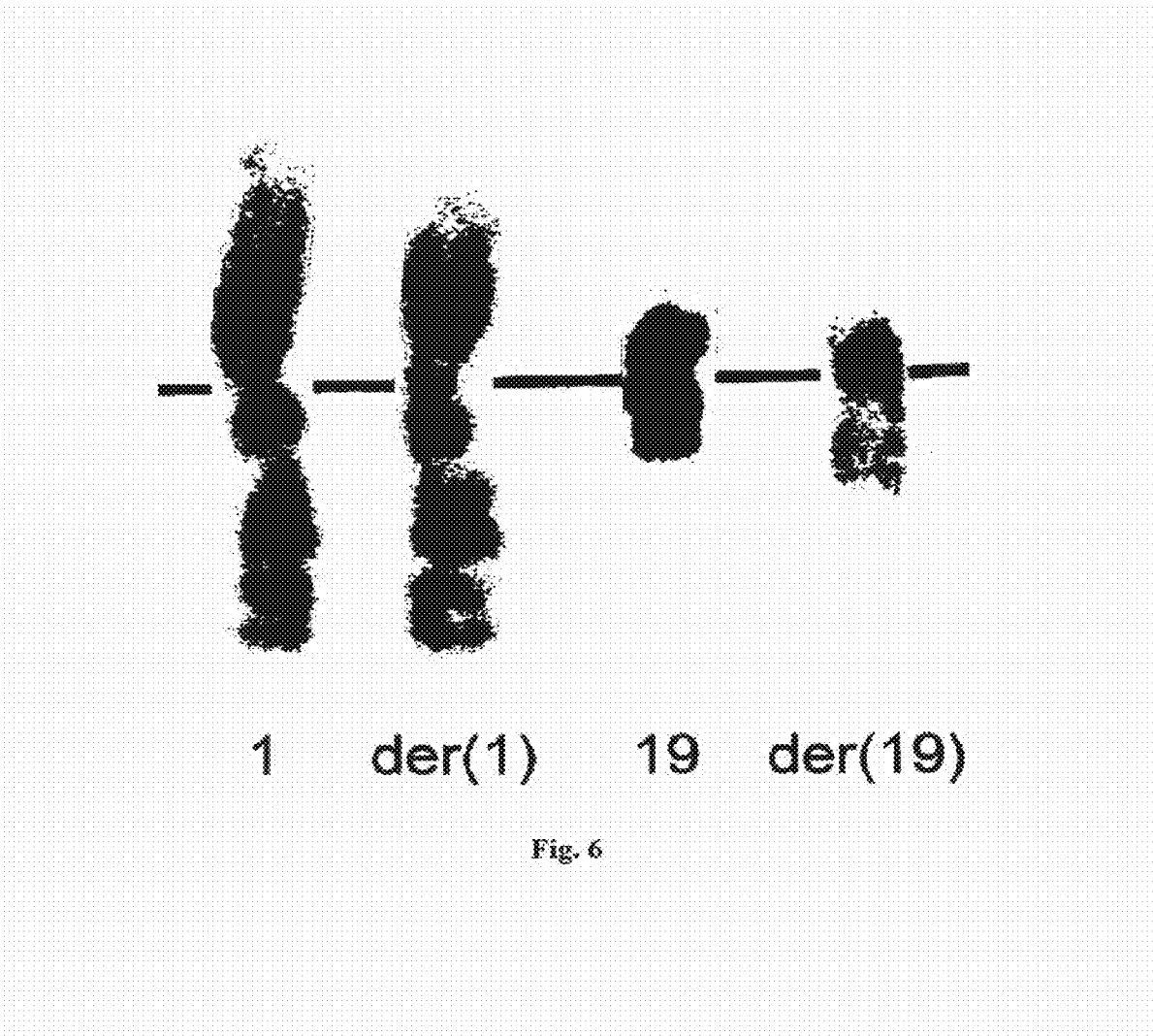

FIG. 6: Partial karyotype of cell line S40.2. Partial G-banded karyotype showing chromosome 1 and 19 as well as their derivatives resulting from t(1;19)(p35.2;q13.4).

Figure 7:
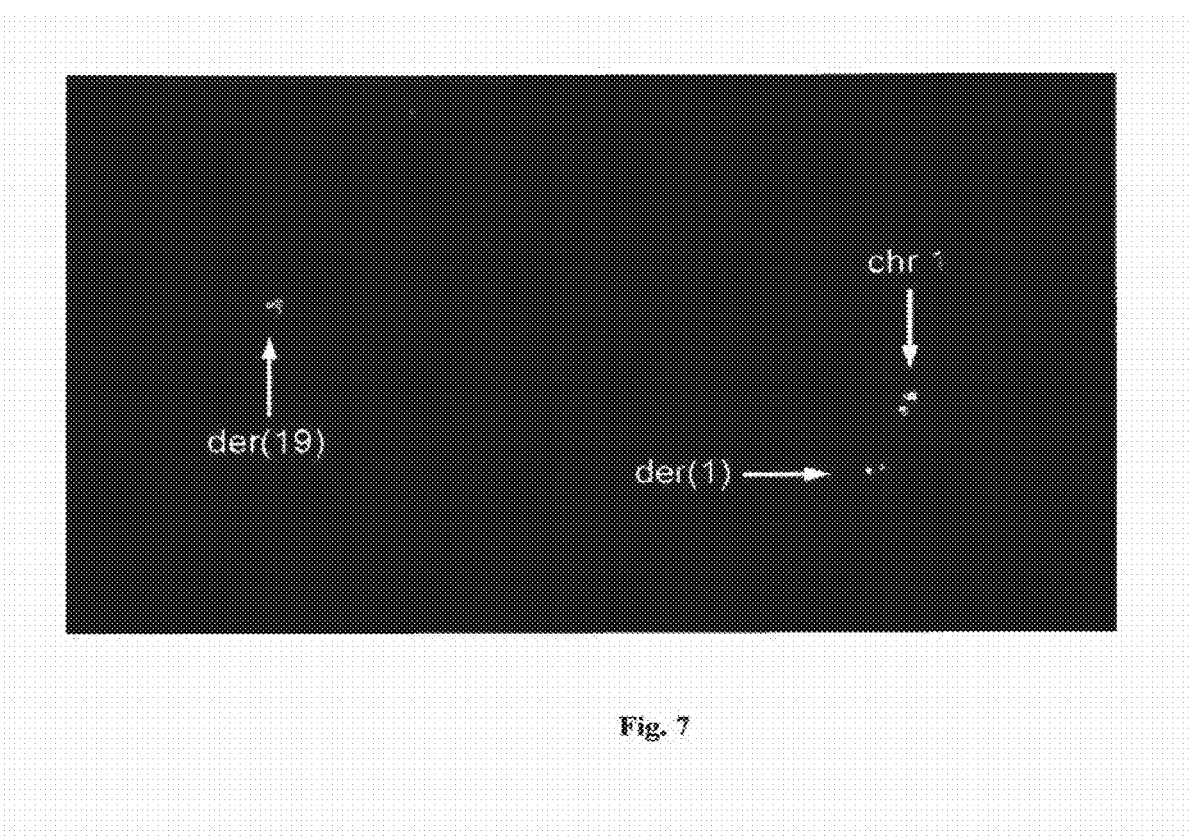

FIG. 7: Delineation of PUM1 breakpoint by metaphase FISH. Part of metaphase of cell line S40.2 after FISH with two overlapping BAC clones RP11-201O14 and RP11-1136E4 both spanning the whole genomic sequence of PUM1 in 1p35.2. The breakpoint in 1p35.2 is located within PUM1 indicated by a separation of RP11-201O14 and RP11-1136E4. Because of weak remaining signals of RP11-1136E4 on the der(1) the breakpoint is located within RP11-1136E4 distal to RP11-201O14.

Figure 8:
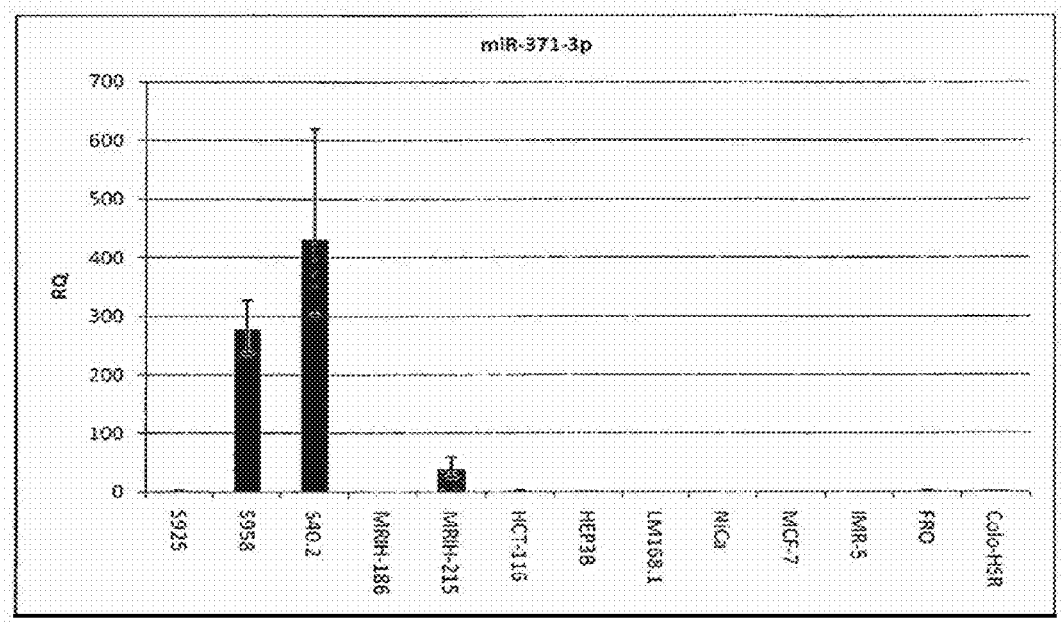

FIG. 8: Relative expression of miR-371-3p. Relative expression of miR-371-3p was determined by real-time PCR (mean s.d. from three independent experiments). Ct values were normalized to miR-103.

Figure 9:
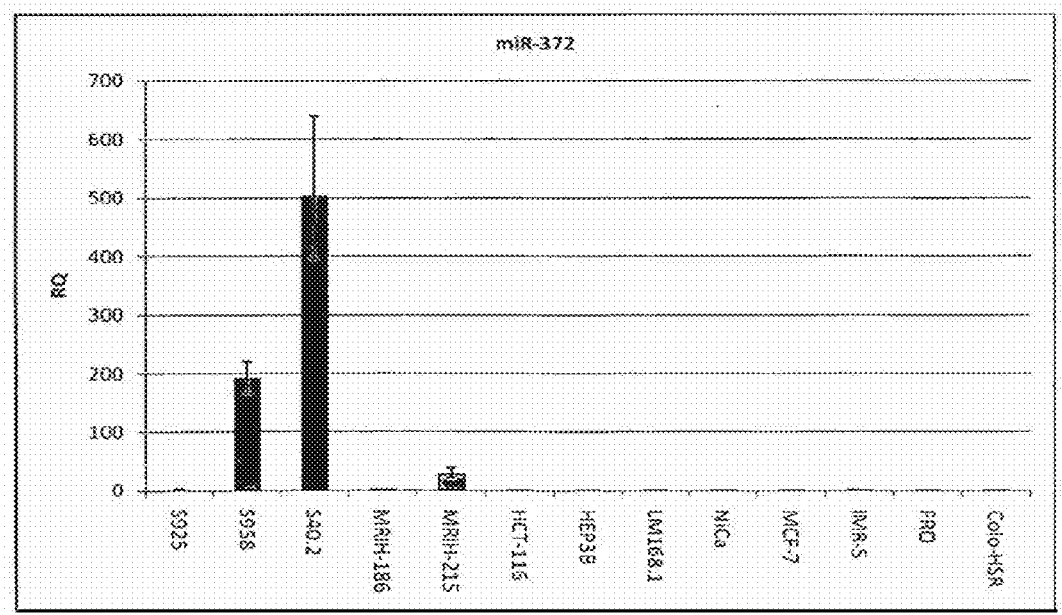

FIG. 9: Relative expression of miR-372. Relative expression of miR-372 was determined by real-time PCR (mean s.d. from three independent experiments). Ct values were normalized to miR-103.

Figure 10:
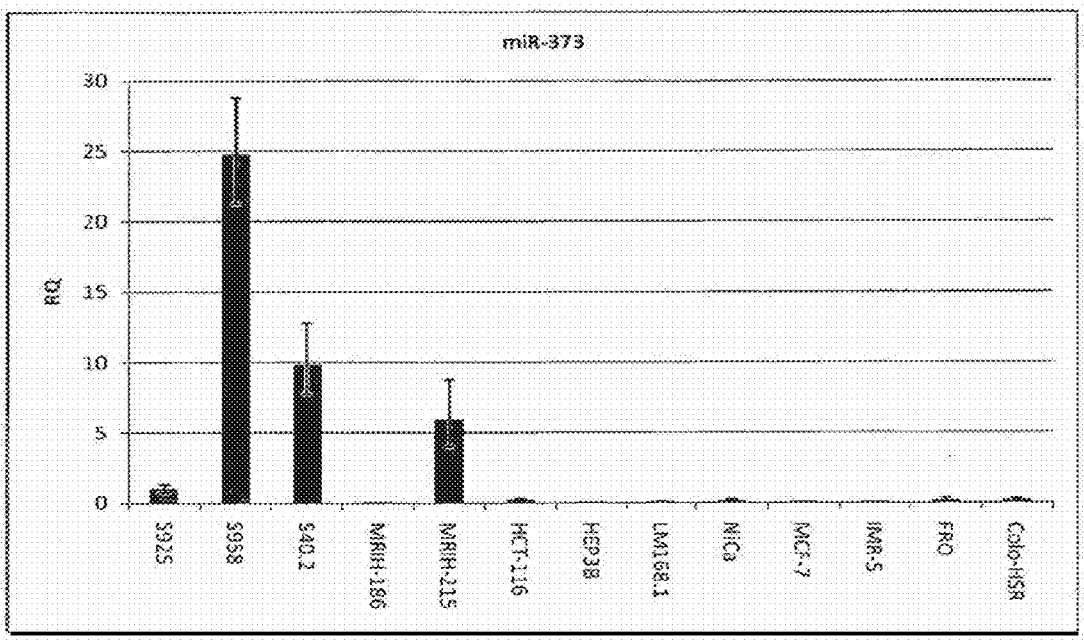

FIG. 10: Relative expression of miR-373. Relative expression of miR-373 was determined by real-time PCR (mean s.d. from three independent experiments). Ct values were normalized to miR-103.

Figure 11:
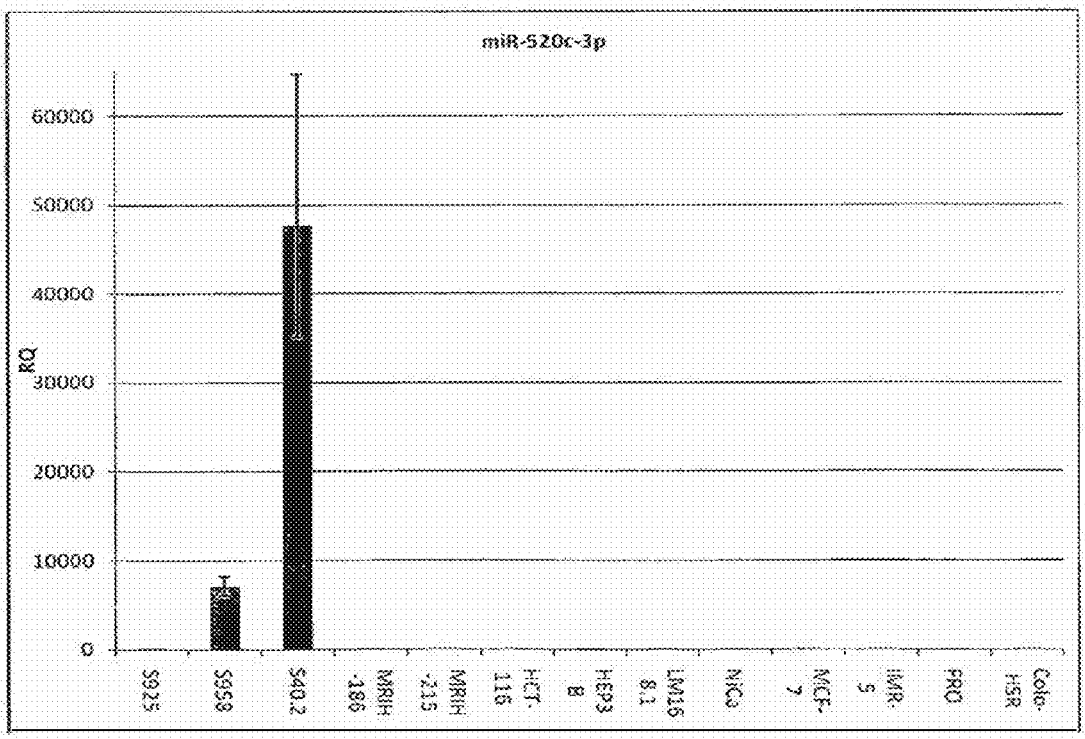

FIG. 11: Relative expression of miR-520c.3p. Relative expression of miR-520c-3p was determined by real-time PCR (mean s.d. from three independent experiments). Ct values were normalized to miR-103.

Figure 12:
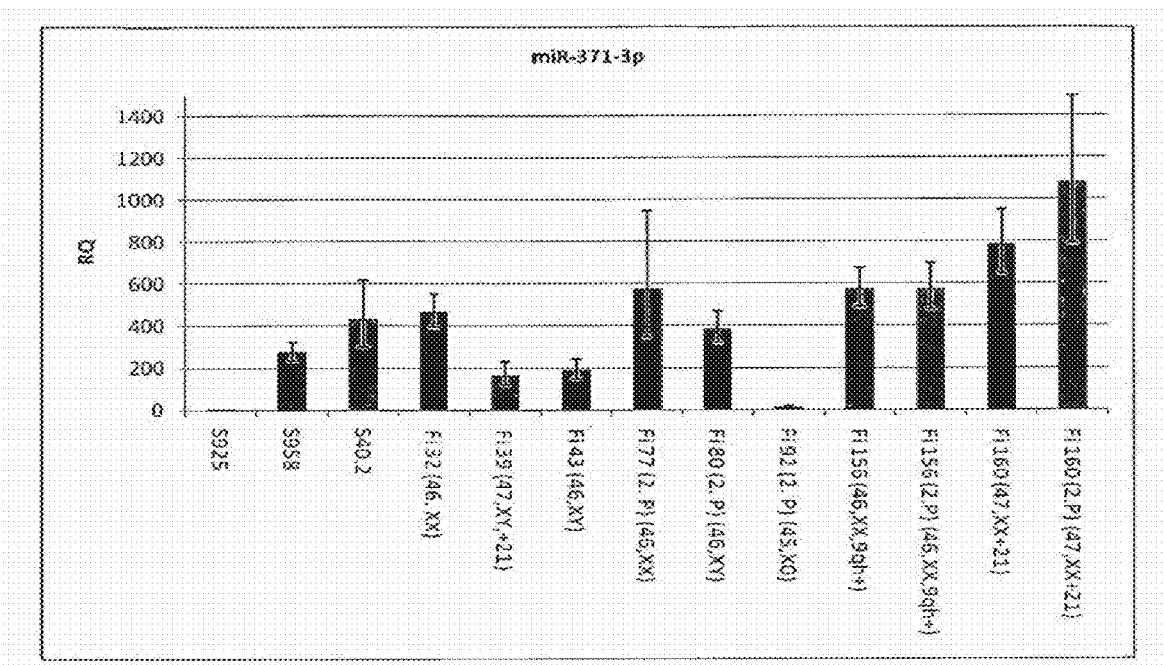

FIG. 12: Relative expression of miR-371-3p. Relative expression of miR-371-3p was determined by real-time PCR (mean s.d. from three independent experiments). Ct values were normalized to miR-103. Karyotypes of the chorionic villi are shown in parentheses.

Figure 13:
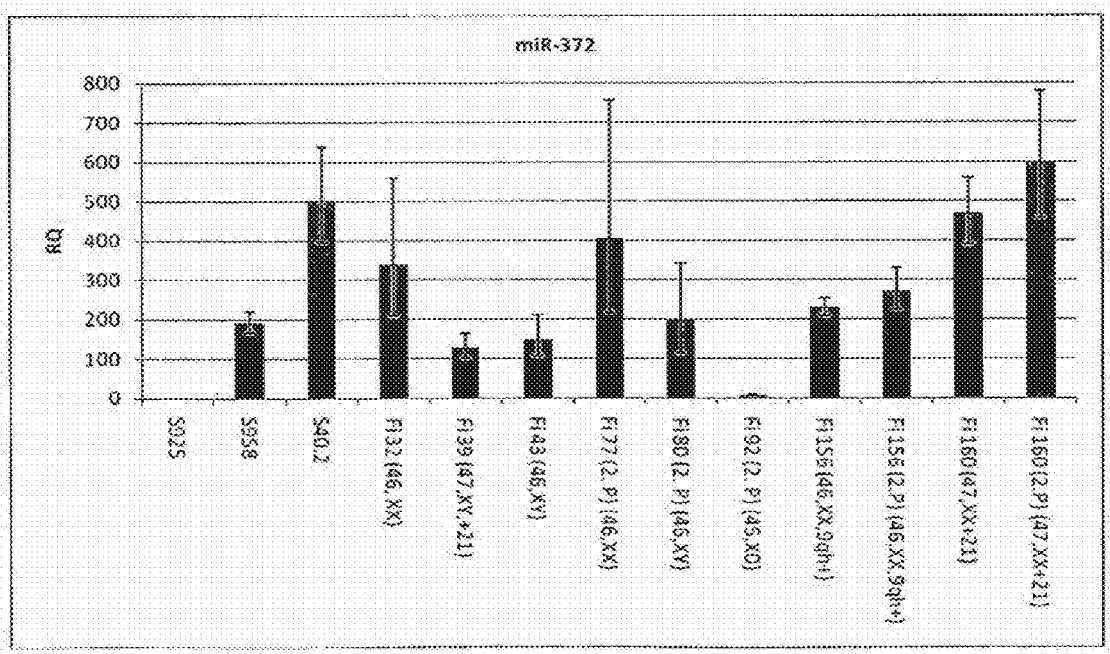

FIG. 13: Relative expression of miR-372. Relative expression of miR-372 was determined by real-time PCR (mean s.d. from three independent experiments). Ct values were normalized to miR-103.

Figure 14:
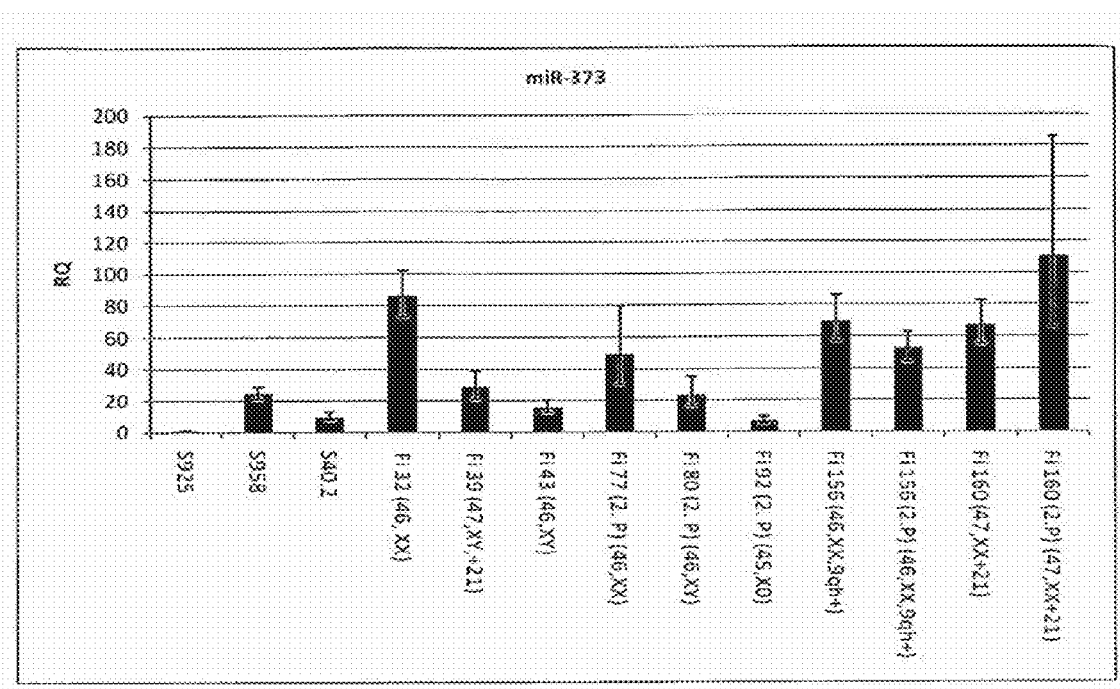

FIG. 14: Relative expression of miR-373. Relative expression of miR-373 was determined by real-time PCR (mean s.d. from three independent experiments). Ct values were normalized to miR-103.

Figure 15:
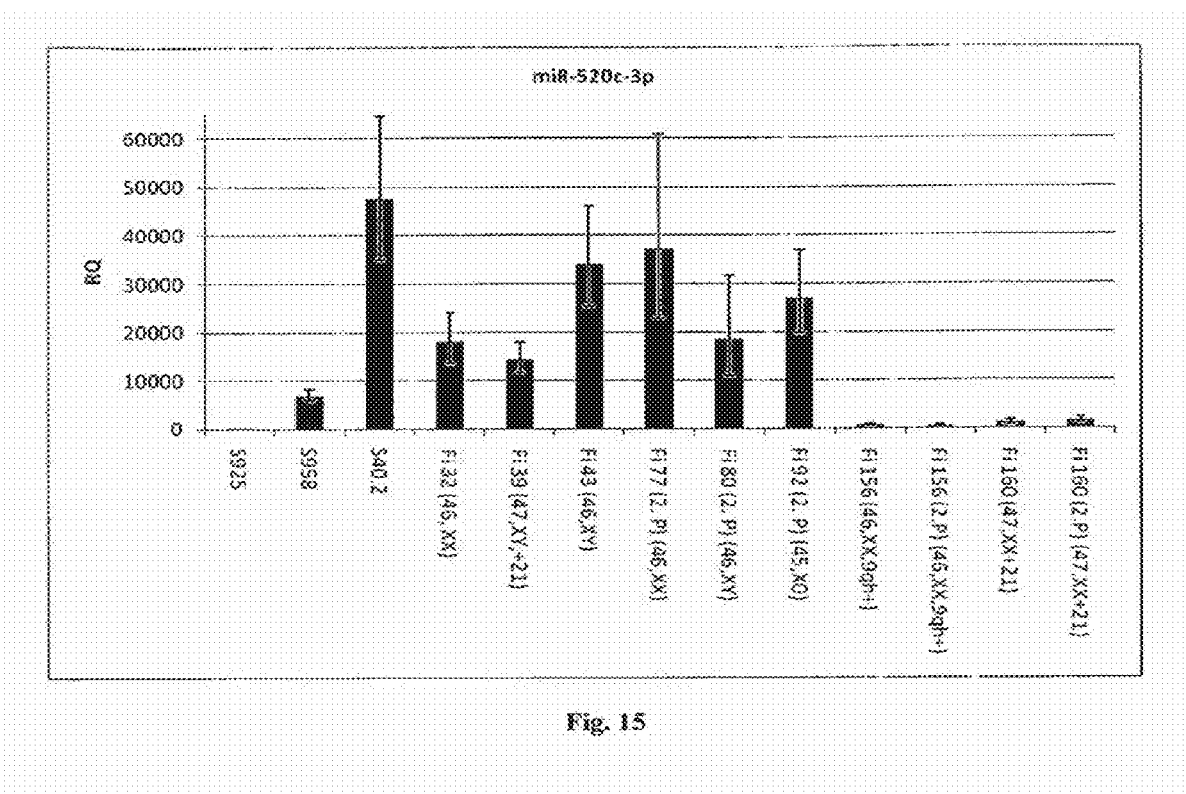

FIG. 15: Relative expression of miR-520c-3p. Relative expression of miR-520c-3p in two thyroid adenoma tissues (one without 19q13.4 rearrangement (S925) and one with 19q13.4 rearrangement (S958)), one cell line derived from thyroid adenoma with 19q13.4 rearrangement (S40.2) as well as eight different cultured chorionic villi (first and/or second passage) was determined by real-time PCR (mean s.d. from three independent experiments). Ct values were normalized to miR-103.

DETAILED DESCRIPTION OF THE INVENTION

The present invention is directed to compositions and methods relating to preparation and characterization of miR-NAs, as well as use of miRNAs for therapeutic, prognostic, and diagnostic applications in tumors which develop because of a chromosomal rearrangement, in particular chromosomal translocation.

The present invention based on and illustrated by thyroid adenomas that are common human tumors with a high prevalence even in iodine sufficient areas. Rearrangements of chromosomal band 19q13.4 are frequently found in thyroid adenomas making them the most frequent specific chromosomal translocations in human epithelial tumors at all (Belge et al., Cancer Genet. Cytogenet. 101 (1998), 42-48). Two microRNA (miRNA) gene clusters i.e. C19MC and miR-371-3 are located in close proximity to the breakpoint region of these chromosomal rearrangements. The stem cell associated microRNAs miR-520c and miR-373 are members of these clusters and have been implicated in invasive growth of epithelial cells in vitro and in vivo (Huang et al., Nat. Cell Biol. 10 (2008), 202-210).

The concept of a role of microRNAs in tumorigenesis has been addressed by, e.g., Calin et al. 2002, who in 2004 have shown an association between the breakpoints seen in chromosomal rearrangements and the assignment of genes encoding microRNA (Calin et al., Proc. Natl. Acad. Sci. USA 99 (2002), 15524-15529; Calin et al., Proc. Natl. Acad. Sci. USA 101 (2004), 2999-3004). Moreover, the activation of a cellular proto-oncogene, i.e. c-myc due to its near location to a miRNA-locus has been described (Calin et al. (2004), supra; Gauwerky et al., Proc. Natl. Acad. Sci. USA 86 (1989), 8867-

8871). However, so far no example of a translocation leading to the activation of oncogenic microRNAs has been shown or envisaged although the coincidence between breakpoints seen in chromosomal rearrangements and the location of miRNA genes has been known; see, e.g., Calin and Croce, J. Clin. Invest. 117 (2007), 2059-2066.

Experiments performed within the scope of the present invention surprisingly revealed that by rearrangements of chromosomal band 19q13.4 both the C19MC and miR-371-3 cluster become consistently activated thus allowing delineating a distinct molecular subtype of thyroid adenomas. In view of the frequent occurrence of rearrangements of 19q13.4 in human neoplasias the present inventors are currently of the opinion that activation of both clusters is a more general phenomenon in human neoplasias and that altered expression of miRs may be significant in tumors involving other chromosomal arrangements as well.

Accordingly, the present invention relates to methods of diagnosing whether a subject has, or is at risk for developing a tumor preferably involving a chromosomal rearrangement comprising measuring the level of at least one microRNA (miR) in a test sample from the subject, wherein the presence or increased level of the miR in the test sample, relative to the level of a corresponding miR in a control sample, is indicative of the subject either having, or being at risk for developing said tumor.

Furthermore, the present invention relates to pharmaceutical compositions for treating a subject suffering from a tumor preferably involving a chromosomal rearrangement, said composition comprising a compound capable of inhibiting expression of at least one miR as defined in any one of the preceding claims or as defined herein and more specifically in Table 1, or decreasing the amount or level of activity of the miR; and optionally a pharmaceutically acceptable carrier.

In addition, the present invention relates to methods of inhibiting proliferation of a cell of a tumor preferably involving a chromosomal rearrangement comprising:
(i) introducing into the cell one or more agents which inhibit expression or activity of one or more miRs which expression is induced or increased in the tumor cell preferably having a chromosomal rearrangement, relative to a control cell; and
(ii) maintaining the cell under conditions in which the one or more agents inhibits expression or activity of the miR, thereby inhibiting proliferation of the tumor cell.

It is within the present invention that the tumor subject to each and any of the methods, processes and/or uses disclosed herein is a benign or malignant tumor. In an embodiment the tumor is a tumor of the thyroid or a thyroid hyperplasia, a malignant cancer of the breast, a benign or malignant germ line tumor or an ovarian cancer.

Furthermore, the present invention relates to methods for diagnosing or determining a condition of the placenta and/or a pregnancy disorder, wherein the method comprises measuring the level of at least one microRNA (miR) in a test sample from the subject, wherein the presence or increased level of the miR in the test sample, relative to the level of a corresponding miR in a control sample, is indicative of the subject either having, or being at risk for developing said condition of the placenta and/or pregnancy disorder. In an embodiment thereof the miR is a miR as disclosed herein, preferably the miR belongs to a miR cluster, whereby preferably the miR cluster is selected from the group comprising the C19MC cluster and the miR-371-3 cluster, and more preferably a miR of table 1. In an embodiment the placenta and/or pregnancy disorder is selected from the group comprising pre-eclampsia, intrauterine growth retardation, placenta moles and their remnants. In another embodiment the method is for the diagnosis of a chromosomal aberration of a fetus. In a more preferred embodiment, the chromosomal aberreation is a missing X-chromosome or trisomy 21.

The present invention also relates to methods of identifying an anti-tumor agent for a tumor, comprising providing a test agent to a cell and measuring the level of at least one miR associated with increased expression levels in tumor cells preferably having a chromosomal rearrangement, wherein a decrease in the level of the miR in the cell, relative to a suitable control cell, is indicative of the test agent being an anti-tumor agent.

Further, the present invention relates to kits useful in methods of the present invention concerning the diagnosis of tumors preferably having a chromosomal rearrangement and the identification of anti-tumor agents therefore, comprising one or more reagents for detecting one or more miRs as described herein.

Methods for detecting the presence of miR are known to a person skilled in the art and, for example, described in Cissell K A, Deo S K (2009) Trends in microRNA detection. Anal Bioanal Chem 394: 1109-1116, or, by means of miRNA-FISH, e.g., using locked nucleic acid (LNA) probes, see Nuovo G J, Elton T S, Nana-Sinkam P, Volinia S, Croce C M, Schmittgen T D. A methodology for the combined in situ analyses of the precursor and mature forms of microRNAs and correlation with their putative targets. Nat. Protoc. 2009; 4(1):107-15, or Song R, Ro S, Michaels J D, Park C, McCarrey J R, Yan W. Many X-linked microRNAs escape meiotic sex chromosome inactivation. Nat Genet. 2009 April; 41(4): 488-93. Epub 2009 Mar. 22; or by means of Northern blot see, e.g., Valoczi A, Hornyik C, Varga N, Burgyan J, Kauppinen S, et al. (2004) Sensitive and specific detection of microRNAs by northern blot analysis using LNA-modified oligonucleotide probes. Nucleic Acids Res 32: e175.

As to the C19M cluster it is to be acknowledged that it was first described in Bentwich I, Avniel A, Karov Y, Aharonov R, Gilad S, et al. (2005) Identification of hundreds of conserved and nonconserved human microRNAs. Nat Genet 37: 766-770, and referred to as C19MC for the first time in Lehnert S, Van Loo P, Thilakarathne P J, Marynen P, Verbeke G, et al. (2009) Evidence for co-evolution between human microRNAs and Alu-repeats. PLoS ONE 4: e4456.

Unless specifically stated otherwise, the terms "cancer" and "tumor" are used interchangeably herein.

As used herein interchangeably, a "miR," "microRNA," "miR," or "miRNA" refers to the unprocessed or processed RNA transcript from an miR gene. As the miRs are not translated into protein, the term "miRs" does not include proteins. The unprocessed miR gene transcript is also called an "miR precursor", and typically comprises an RNA transcript of about 70-100 nucleotides in length. The miR precursor can be processed by digestion with an RNAse (for example, Dicer, Argonaut, or RNAse 111, e.g., *E. coli* RNAse 111) into an active 19-25 nucleotide RNA molecule. This active 19-25 nucleotide RNA molecule is also called the "processed" miR gene transcript or "mature" miRNA. It is to be understood that the term "miR" as used herein can include one or more of miR-oligonucleotides, including mature miRs, pre-miRs, pri-miRs, or a miR seed sequence. In certain embodiments, a mixture of various miR nucleic acids can also be used. Also, in certain embodiments, the miRs may be modified to enhance delivery.

The miRNA (miR) information is available from the Sanger Institute, which maintains a registry of miRNA at http:/microrna.sanger.ac.uk/sequences/. (see also: Griffiths-Jones S, et al., "miRBase: tools for microRNA genomics.

NAR 2008 36 (Database Issue): D154-D158; Griffiths-Jones S, et al. "miRBase: microRNA sequences, targets and gene nomenclature." NAR 2006 34(Database Issue): D140-D144 or Griffiths-Jones S., "The microRNA Registry.", NAR 2004 32(Database Issue): D109-D111.) The miRBase Sequence database includes the nucleotide sequences and annotations of published miRNA from a variety of sources. The miRBase Registry provides unique names for novel miRNA genes that comply with conventional naming nomenclature for new miRNA prior to publication. Also, the miRBase Targets is a resource for predicated miRNA targets in animals.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAase 111). It is understood that the active 19-25 nucleotide RNA molecule can also be produced directly by biological or chemical synthesis, without having been processed from the miR precursor.

The present invention encompasses methods of diagnosing whether a subject has, or is at risk for developing, tumor, comprising measuring the level of at least one miR in a test sample from the subject and comparing the level of the miR in the test sample to the level of a corresponding miR in a control sample. As used herein, a "subject" can be any mammal that has, or is suspected of having, tumor involving a chromosomal rearrangement, in particular a translation in chromosome 19; see also the Examples. In a particular embodiment, the subject is a human who has, or is suspected of having, tumor. Preferred miRs to be used in the methods and kits of the present invention are set forth in Table 1 below:

TABLE 1 microRNAs of cluster C19MC and miR371-3

| name | typ | sequenz | mirBase acc # |
|---|---|---|---|
| hsa-mir-371 | Stem-loop | ```
              cu   g          u     c
guggcacucaaa   gugg  ggcacuuuc gcu  u
||||||||||||   ||||  ||||||||| |||
cauugugaguuu   uacc  ccgugaaag ugg  c
              uc   g          -     u
``` | MI0000779 |
| hsa-miR-371-3p | mature | aagugccgccaucuuuugagugu | MIMAT0000723 |
| hsa-miR-371-5p | mature | acucaaacugugggggcacu | MIMAT0004687 |
| Hsa-mir-372 | Stem-loop | ```
gug   -         g  -      a      gaug
   ggc  cucaaaugu g agcacu uucu       u
   |||  ||||||||| | |||||| ||||       c
   cug  gaguuuaca c ucguga aagg       c
-ca   c         g  g      -     ugaa
``` | MI0000780 |
| hsa-miR-372 | mature | aaagugcugcgacauuugagcgu | MIMAT0000724 |
| hsa-mir-373 | Stem-loop | ```
           -     g        uuuuug
ggauaacuc  aaaau  ggggcgcuuucc      u
|||||||||  |||||  ||||||||||||      
cccuguggg  uuuua  cuucgugaaggg      c
           g     g        ucaugu
``` | MI0000781 |
| hsa-miR-373 | mature | gaagugcuucgauuuggggugu | MIMAT0000726 |
| hsa-miR-373* | minor | acucaaaauggggcgcuuucc | MIMAT0000725 |
| hsa-mir-512-1 | Stem-loop | ```
u     ug  ca     cu  g        ----    g
 cucaguc  ugg  cucagc  uga ggcacuu    ucug u
 |||||||  |||  ||||||  |||  |||||||    ||||
 gagucag  acc  gagucg  acu ucgugaa    agac g
g     ua  ug     au  g        agua    c
``` | MI0003140 |
| hsa-miR-512-5p | mature | cacucagccuugagggcacuuuc | MIMAT0002822 |
| hsa-miR-512-3p | mature | aagugcugucauagcugagguc | MIMAT0002823 |
| hsa-mir-512-2 | Stem-loop | ```
a  --    ug  ca     cu  g        ----     g
 ggu cuu  cucaguc  ugg  cucagc  uga ggcacuu    ucug u
 ||| |||  |||||||  |||  ||||||  |||  |||||||    ||||
 cca gag  gagucag  acc  gagucg  acu ucgugaa    agac g
 c   cg    ua  ug     au  g        agua    c
``` | MI0003141 |
| hsa-miR-512-5p | mature | cacucagccuugagggcacuuuc | MIMAT0002822 |

TABLE 1-continued microRNAs of cluster C19MC and miR371-3

| name | typ | sequenz | mirBase acc # |
|---|---|---|---|
| hsa-miR-512-3p | mature | aagugcugucauagcugagguc | MIMAT0002823 |
| hsa-mir-515-1 | Stem-loop | ```
     u    c  u           a    uu    gu
ucuca gcagu au cuccaaaagaa gcac  ucuguu  c
||||| ||||| || |||||||||||| ||||  ||||||  u
agagu uguca ug gagguuucuu cgug  agacga  g
     u    c           c    --    aa
``` | MI0003144 |
| hsa-miR-515-5p | mature | uucuccaaaagaaagcacuuucug | MIMAT0002826 |
| hsa-miR-515-3p | mature | gagugccuucuuuuggagcguu | MIMAT0002827 |
| hsa-mir-515-2 | Stem-loop | ```
     u    c  u           a    uu    gu
ucuca gcagu au cuccaaaagaa gcac  ucuguu  c
||||| ||||| || |||||||||||| ||||  ||||||  u
agagu uguca ug gagguuucuu cgug  agacga  g
     u    c           c    --    aa
``` | MI0003147 |
| hsa-miR-515-5p | mature | uucuccaaaagaaagcacuuucug | MIMAT0002826 |
| hsa-miR-515-3p | mature | gagugccuucuuuuggagcguu | MIMAT0002827 |
| hsa-mir-516a-1 | Stem-loop | ```
                 c  aaa         guug u
ucucaggcugugaccuucu gagg  gaagcacuuucu  uc g
|||||||||||||||||||| ||||  ||||||||||||  || a
agaguuuggcaugggaga uuuc  cuucgugaaaga  ag a
                 c  ---         --aa a
``` | MI0003180 |
| hsa-miR-516a-5p | mature | uucucgaggaaagaagcacuuuc | MIMAT00047 |
| hsa-miR-516a-3p | mature | ugcuuccuuucagagggu | MIMAT0006778 |
| hsa-mir-516a-2 | Stem-loop | ```
     gg          c   aaa         guug u
ucuca  uugugaccuucu gagg  gaagcacuuucu  uc g
|||||  ||||||||||| ||||  ||||||||||||  || a
agagu  ggcaugggaga uuuc  cuucgugaaaga  ag a
     uu          c   ---         --aa a
``` | MI0003181 |
| hsa-miR-516a-5p | mature | uucucgaggaaagaagcacuuuc | MIMAT0004770 |
| hsa-miR-516a-3p | mature | ugcuuccuuucagagggu | MIMAT0006778 |
| hsa-mir-516b-1 | Stem-loop | ```
        cu   a      uaa         g     g
ucucagg gugacc ucuggagg  gaagcacuuucu uuuu u
|||||||| |||||| ||||||||  |||||||||||| |||| g
agaguuu cauugg agacuuuc  cuucgugaaaga aaga a
        cu   g      ---         a     a
``` | MI0003172 |
| hsa-miR-516b | mature | aucuggagguaagaagcacuuu | MIMAT0002859 |
| hsa-miR-516b* | minor | ugcuuccuuucagagggu | MIMAT0002860 |
| hsa-mir-518b | Stem-loop | ```
     -u  u   a       uaa        g guuu
ucuca  ga gugacc ucuggagg  gaagcacuuu  u
|||||  || |||||| ||||||||  |||||||||| 
agagu  cu cauugg agacuuuc  cuucgugaaa  g
     uu  -   g       ---        g aagu
``` | MI0003167 |
| hsa-miR-516b | mature | aucuggagguaagaagcacuuu | MIMAT0002859 |
| hsa-miR-516b* | minor | ugcuuccuuucagagggu | MIMAT0002860 |

TABLE 1-continued microRNAs of cluster C19MC and miR371-3

| name | typ | sequenz | mirBase acc # |
|---|---|---|---|
| hsa-mir-517a | Stem-loop | ```
                        c    u   a    u    g  g a
       ucucaggcagugac cucuaga gga gcac gucu uu u  u
       |||||||||||||| ||||||| ||| |||| |||| || |  a
       agaguuugucauug gagauuu ccu cgug uaga aa a  a
                        u    c   a    c    a  g a
``` | MI0003161 |
| hsa-miR-517a | mature | aucgugcaucccuuuagagugu | MIMAT0002852 |
| hsa-miR-517* | minor | ccucuagauggaagcacugucu | MIMAT0002851 |
| hsa-mir-517b | Stem-loop | ```
             c    u   a    u    guugu
       gugac cucuaga gga gcac gucu    c
       ||||| ||||||| ||| |||| ||||    u
       cauug gagauuu ccu cgug uaga    a
             u    c   a    c    aaaga
``` | MI0003165 |
| hsa-miR-517b | mature | ucgugcaucccuuuagaguguu | MIMAT0002857 |
| hsa-miR-517* | minor | ccucuagauggaagcacugucu | MIMAT0002851 |
| hsa-mir-517c | Stem-loop | ```
       gaaga               c    u   a    u    guugu
             ucucaggcagugac cucuaga gga gcac gucu    c
             |||||||||||||| ||||||| ||| |||| ||||    u
             agaguuugucauug gagauuu ccu cgug uaga    a
       cuaaa               u    c   a    c    aaaga
``` | MI0003174 |
| hsa-miR-517c | mature | aucgugcauccuuuagagugu | MIMAT0002866 |
| hsa-miR-517* | minor | ccucuagauggaagcacugucu | MIMAT0002851 |
| hsa-mir-518a-1 | Stem-loop | ```
                        -  -       c     g g c
       ucucaagcuguga cu gcaaagggaagc cuuucu uu u u
       |||||||||||||| || |||||||||||| |||||| || | g
       agaguuuggcauu gg cguuucccuucg gaaaga aa a a
                        a  u       c     g g a
``` | MI0003170 |
| hsa-miR-518a-5p | mature | cugcaaagggaagcccuuuc | MIMAT0005457 |
| hsa-miR-518a-3p | mature | gaaagcgcuucccuuugcugga | MIMAT0002863 |
| hsa-mir-518a-2 | Stem-loop | ```
                        g  -       c     g g c
       ucucaagcugugg ucu gcaaagggaagc cuuucu uu u u
       |||||||||||| ||| |||||||||||| |||||| || | a
       agaguuuggcauu agg cguuucccuucg gaaaga aa a a
                        -  u       c     g g a
``` | MI0003173 |
| hsa-miR-518a-5p | mature | cugcaaagggaagcccuuuc | MIMAT0005457 |
| hsa-miR-518a-3p | mature | gaaagcgcuucccuuugcugga | MIMAT0002863 |
| hsa-mir-518b | Stem-loop | ```
           u   gc   c    a       uc   g  u
       uca gcugug ccuc agaggg agcgcuu uguu uc g
       ||| |||||| |||| |||||| ||||||| |||| ||
       agu uggcau ggag uuuccc ucgcgaa acaa ag a
           u   uu   a    c       --   a  a
``` | MI0003156 |
| hsa-miR-518b | mature | caaagcgcuccccuuuagaggu | MIMAT0002844 |

TABLE 1-continued microRNAs of cluster C19MC and miR371-3

| name | typ | sequenz | mirBase acc # |
|---|---|---|---|
| hsa-mir-518c | Stem-loop | (see below) | MI0003159 |

```
          gcgagaaga     u            u             a    uc   g    u
     ucuca     gcugugac cucuggagggaagc cuu  uguu uc  g
     |||||     |||||||| |||||||||||||| |||  |||| ||  a
     agagu     uggcauug gagauuucucuucg gaa  acaa ag  a
     ----cgaaa     u            u             c    --   a    a
```

| name | typ | sequenz | mirBase acc # |
|---|---|---|---|
| hsa-miR-518c | mature | caaagcgcuucucuuuagagugu | MIMAT0002848 |
| hsa-miR-518c* | minor | ucucuggagggaagcacuuucug | MIMAT0002847 |
| hsa-mir-518d | Stem-loop | (see below) | MI0003171 |

```
        c  u       c           a      cu   g    u
     uc ca gcugugac cucuagagggaagc cuuu guu uc g
     || || |||||||| |||||||||||||| |||| ||| || a
     ag gu uggcauug gagguucccuucg gaaa caa ag a
        a  u       c           c      -c   -    a
```

| name | typ | sequenz | mirBase acc # |
|---|---|---|---|
| hsa-miR-518d-5p | mature | cucuagagggaagcacuuucug | MIMAT0005456 |
| hsa-miR-518d-3p | mature | caaagcgcuucccuuuggagc | MIMAT0002864 |
| hsa-mir-518e | Stem-loop | (see below) | MI0003169 |

```
          -  ug   c    ag                guugc
     ucucag gc ugac cucu agggaagcgcuuucu       u
     |||||| || |||| |||| ||||||||||||||      a
     agaguu cg auug gaga ucccuucgcgaaaga       a
          u  ca   u    cu                aaagaa
```

| name | typ | sequenz | mirBase acc # |
|---|---|---|---|
| hsa-miR-518e | mature | aaagcgcuucccuucagagug | MIMAT0002861 |
| hsa-miR-518e* | minor | cucuagagggaagcgcuuucug | MIMAT0005450 |
| hsa-mir-518f | Stem-loop | (see below) | MI0003154 |

```
          ugcu     c           a       ---    gu
     ucuca     guga ccucuagagggaagc cuuuc  ucuu  c
     |||||     |||| |||||||||||||| |||||  ||||
     agagu     cauu ggagauuucucuucg gaaag  agaa u
          uucu     a           c       aaa    aa
```

| name | typ | sequenz | mirBase acc # |
|---|---|---|---|
| hsa-miR-518f | mature | gaaagcgcuucucuuuagagg | MIMAT0002842 |
| hsa-miR-518f* | minor | cucuagagggaagcacuuucuc | MIMAT0002841 |
| hsa-mir-519a-1 | Stem-loop | (see below) | MI0003178 |

```
            u              a          guug  u
     cucaggc gugacacucuagaggga gcgcuuucu    uc g
     ||||||| |||||||||||||||||| |||||||||    || a
     gaguuug cauugugagauuucccu cgugaaagg    ag a
            u              a          --aa  a
```

| name | typ | sequenz | mirBase acc # |
|---|---|---|---|
| hsa-miR-519a | mature | aaagugcauccuuuuagagugu | MIMAT0002869 |
| hsa-miR-519a* | minor | cucuagagggaagcgcuuucug | MIMAT0005452 |
| hsa-mir-519a-2 | Stem-loop | (see below) | hsa-mir-519a-2 |

```
            u  u c   c    a           guug  u
     ucucaggc gug c cucua aggga gcgcuuucu    uc g
     |||||||| ||| | ||||| ||||| |||||||||    || a
     agaguuug cau g ggagau uucca cgugaaagg    ag a
            u  u u   u    a           --aa  a
```

| name | typ | sequenz | mirBase acc # |
|---|---|---|---|
| hsa-miR-519a | mature | aaagugcauccuuuuagagugu | MIMAT0002869 |
| hsa-mir-519b | Stem-loop | (see below) | MI0003151 |

```
        u  u   c    a           guug  u
     ca gc guga ccucuagaggga gcgcuuucu    uc g
     || || |||| ||||||||||||| |||||||||    || a
     gu ug cauu ggagauuuccu cgugaaaga    ag a
        u  u   u    a                --aa  a
```

TABLE 1-continued microRNAs of cluster C19MC and miR371-3

| name | typ | sequenz | mirBase acc # |
|---|---|---|---|
| hsa-miR-519b-5p | mature | cucuagagggaagcgcuuucug | MIMAT0005454 |
| hsa-miR-519b-3p | mature | aaagugcauccuuuuagagguu | MIMAT0002837 |
| hsa-mir-519c | Stem-loop | ```
       c      c        a           guug  u
ucucag cuguga ccucuagagggga gcgcuuucu    uc g
|||||| |||||| |||||||||||||| |||||||||   || a
agaguu gacauu ggagauuuucu  cgugaaaga    ag a
       u      a         a         --aa  a
``` | MI0003148 |
| hsa-miR-519c-5p | mature | cucuagagggaagcgcuuucug | MIMAT0002831 |
| hsa-miR-519c-3p | mature | aaagugcaucuuuuagaggau | MIMAT0002832 |
| hsa-mir-519d | Stem-loop | ```
     u   u   c  c    a       uc    uuu
uccca gc gugac cuc aaaggga gcgcuu uguuug  u
||||| || ||||| ||| ||||||| |||||| ||||||
agggu ug cauug gag uuucccu cgugaa acaaau c
     u   c   u  a    c       --    ucu
``` | MI0003162 |
| hsa-mir-519d | mature | caaagugccucccuuuagagug | MIMAT0002853 |
| hsa-mir-519e | Stem-loop | ```
      u   c  u   c    ga    uc    ga
ucuca gcagu au cuc aaaagg gcacuu uguuu  a
||||| ||||| || ||| |||||| |||||| |||||
agagu uguca ug gag uuuucc cgugaa acaaa  a
      u   u  a   ac    --    ag
``` | MI0003145 |
| hsa-miR-5193 | mature | aagugccuccuuuuagaguguu | MIMAT0002829 |
| hsa-miR-519e* | minor | uucuccaaaagggagcacuuuc | MIMAT0002828 |
| hsa-mir-520a | Stem-loop | ```
         u  cc                 g  g
cucaggcug gac   uccagagggaaguacuuucu uu ucu
||||||||| |||   |||||||||||||||||||| || ||  g
gaguuuggc uug   agguuucccuucgugaaaga aa aga
         u  uc                 a  g
``` | MI0003149 |
| hsa-miR-520a-5p | mature | cuccagagggaaguacuuucu | MIMAT0002833 |
| hsa-miR-520a-3p | mature | aaagugcuucccuuuggacugu | MIMAT0002834 |
| hsa-mir-520b | Stem-loop | ```
       c             guug  u
cccucua agggaagcgcuuucu    uc g
||||||| ||||||||||||||    || a
gggagau uuccuucgugaaaga    ag a
       u             --aa  a
``` | MI0003155 |
| hsa-miR-520b | mature | aaagugcuuccuuuuagaggg | MIMAT0002843 |
| hsa-mir-520c | Stem-loop | ```
       u  cg              guug  u
ucucaggc gu  uccucuagagggaagcacuuucu    uc g
||||||||| ||  ||||||||||||||||||||||    || a
agaguuug ca  gggagauuuccuucgugaaaga    ag a
       c  uu              --aa  a
``` | MI0003158 |
| hsa-miR-520c-5p | mature | cucuagagggaagcacuuucug | MIMAT0005455 |
| hsa-miR-520c-3p | mature | aaagugcuuccuuuuagagggu | MIMAT0002846 |

TABLE 1-continued microRNAs of cluster C19MC and miR371-3

| name | typ | sequenz | mirBase acc # |
|---|---|---|---|
| hsa-mir-520d | Stem-loop | `        g  ua        c      guug  u`<br>`ucucaagcuguga uc  caaagggaagc cuuucu    uc a`<br>`||||||||||||| ||  |||||||||| ||||||    || a`<br>`agaguuuggcauu gg  guuucucuucg gaaaga    ag a`<br>`        g  ug        u      --aa  a` | MI0003164 |
| hsa-miR-520d-5p | mature | cuacaaagggaagcccuuuc | MIMAT0002855 |
| hsa-miR-520d-3p | mature | aaagugcuucucuuuggugggu | MIMAT0002856 |
| hsa-mir-520e | Stem-loop | `    cu  u            u    g      guug    g`<br>`ucuc  gc gugacccucaaga ggaagca uuucu    ucu a`<br>`||||  || ||||||||||||| ||||||| |||||    ||| a`<br>`agag  ug cauggggaguuuu ccuucgu aaaga    agg a`<br>`    uu  u            u    g      ---a    a` | MI0003143 |
| hsa-miR-520e | mature | aaagugcuuccuuuugaggg | MIMAT0002825 |
| hsa-mir-520f | Stem-loop | `      u                    u  gugg  a`<br>`ucucaggc gugacccucuaaagggaagcgcuu cu    uc g`<br>`|||||||| |||||||||||||||||||||||| ||    || a`<br>`agguuuug cauggggagauuuuccuucgugaa ga    ag a`<br>`      c                    c  --aa  a` | MI0003146 |
| hsa-miR-520f | mature | aagugcuuccuuuuagaggguu | MIMAT0002830 |
| hsa-mir-520g | Stem-loop | `     u  u    c    -     uc    guugu`<br>`uccca gc gugac cucuagagg aagcacuu uguuu     c`<br>`||||| || ||||| ||||||||| |||||||| |||||     u`<br>`agggu ug cauug gagauuucc uucgugaa acaaa     g`<br>`     u  c    u    c     --    aaaga` | MI0003166 |
| hsa-miR-520g | mature | acaaagugcuucccuuuagagugu | MIMAT0002858 |
| hsa-mir-520h | Stem-loop | `     u  u    cc    -     uc    guugu`<br>`uccca gc gugac  ucuagagg aagcacuu uguuu     c`<br>`||||| || |||||  ||||||||| |||||||| |||||     u`<br>`agggu ug cauug  agauuuccc uucgugaa acaaa     g`<br>`     u  u    --    c    --    aaaga` | MI0003175 |
| hsa-miR-520h | mature | acaaagugcuucccuuuagagu | MIMAT0002867 |
| hsa-mir-521-1 | Stem-loop | `     g  u  c    c       aa  u    guug  u`<br>`ucuca gc gugac cuc aaagggaag c uucu    uc a`<br>`||||| || ||||| ||| ||||||||| | ||||    || a`<br>`agagu ug cauug gag uuucccuuc g aaga    ag a`<br>`     g  c  u    a       ac  c    --aa  a` | MI0003176 |
| hsa-miR-521 | mature | aacgcacuucccuuuagagugu | MIMAT0002854 |
| hsa-mir-521-2 | Stem-loop | `     g  u  u    c       ---aa    c    gu`<br>`ucucg gc gugac cuc aaagggaag    uuuu ucuu  c`<br>`||||| || ||||| ||| |||||||||    |||| ||||  `<br>`agagu ug cauug gag uuucccuuc    agaa agaa  u`<br>`     g  c  u    a       acgca    a    aa` | MI0003163 |
| hsa-miR-521 | mature | aacgcacuucccuuuagagugu | MIMAT0002854 |
| hsa-mir-522 | Stem-loop | `     -  u  u c          g  c    guug  u`<br>`ucucag gc gug c cucuagagggaa cg uuucu    uc g`<br>`|||||| || ||| | |||||||||||| || |||||    || a`<br>`agaguu cg cau g gagauuucccuu gu aaaga    ag a`<br>`     u  -  u u          g  a    --aa  a` | MI0003177 |
| hsa-miR-522 | mature | aaaaugguucccuuuagagugu | MIMAT0002868 |

TABLE 1-continued microRNAs of cluster C19MC and miR371-3

| name | typ | sequenz | mirBase acc # |
|---|---|---|---|
| hsa-miR-522* | minor | cucuagagggaagcgcuuucug | MIMAT0005451 |
| hsa-mir-523 | Stem-loop | ```
      ugcu          g       u        guug  u
ucuca     gugacccucua agggaagcgc uucu     uc g
|||||     |||||||||||| |||||||||| ||||     || a
agagu     cauugggagau ucccuucgcg aaga     ag a
      uucc          a       c        --aa  a
``` | MI0003153 |
| hsa-miR-523 | mature | gaacgcgcuucccuauagagggu | MIMAT0002840 |
| hsa-miR-523* | minor | cucuagagggaagcgcuuucug | MIMAT0005449 |
| hsa-mir-524 | Stem-loop | ```
      u    c   a   a          cuug
ucuca gcugugac cu caaagggaagc cuuucu    ucca
||||| |||||||| || |||||||||||| ||||||    ||| a
agagu uggcauug ga guuucccuucg ggaaga    agga
      u    u   g   c          --aa
``` | MI0003160 |
| hsa-miR-524-5p | mature | cuacaaagggaagcacuuucuc | MIMAT0002849 |
| hsa-miR-524-3p | mature | gaaggcgcuucccuuuggagu | MIMAT0002850 |
| hsa-mir-525 | Stem-loop | ```
             u   c        u    a     c  aug
cucaagcugugac cuc agaggga gc cuuucu uu    u
|||||||||||||| ||| ||||||| || |||||| ||    g
ggguuuggcauug gag uuucccu cg ggaaga aa    a
             c   a        u    c     a  aaa
``` | MI0003152 |
| hsa-miR-525-5p | mature | cuccagagggaugcacuuucu | MIMAT0002838 |
| hsa-miR-525-3p | mature | gaaggcgcuucccuuuagagcg | MIMAT0002839 |
| hsa-mir-526a-1 | Stem-loop | ```
       cu   c           a        g g  u
cucagg  guga ccucuagagggaagc cuuucu uu cu g
||||||  |||| |||||||||||||||| |||||| || || g
gaguuu  cauu ggagauuuccuucg gaaaga aa ga a
       cu   a           c        g - a
``` | MI0003157 |
| hsa-miR-526a | mature | cucuagagggaagcacuuucug | MIMAT0002845 |
| hsa-mir-526a-2 | Stem-loop | ```
          ag   a   cu   -g g
gugacccucu aggga gca uucu uu a
|||||||||| ||||| ||| |||| || |
cauugggaga uuccu cgu aaga ag a
          cu   a   ac   aa a
``` | MI0003168 |
| hsa-miR-526a | mature | cucuagagggaagcacuuucug | MIMAT0002845 |
| hsa-mir-526b | Stem-loop | ```
       u   c   u                 g g c
ucaggc guga ccucu gagggaagcacuuucu uu u u
|||||| |||| ||||| |||||||||||||||| || | g
agucug cauu ggaga uuccuucgugaaaga aa a a
       u   c   u                 g g a
``` | MI0003150 |
| hsa-miR-526b | mature | cucuugagggaagcacuuucugu | MIMAT0002835 |
| hsa-miR-526b* | minor | gaaagugcuuccuuuuagaggc | MIMAT0002836 |
| hsa-mir-527 | Stem-loop | ```
              --cug       c         guug u
ucucaagcuguga    caaagggaagc cuuuc    uc a
||||||||||||    ||||||||||||| |||||    || a
agaguuuggcauu    guuucccuucg gaaag    ag a
              aagug       u         --aa a
``` | MI0003179 |

TABLE 1-continued microRNAs of cluster C19MC and miR371-3

| name | typ | sequenz | mirBase acc # |
|---|---|---|---|
| hsa-miR-527 | mature | cugcaaagggaagcccuuuc | MIMAT0002862 |

The term mirBase acc # represents the accession number of the indicated sequence in the miRBase database. The miRBase database is a searchable database of published miRNA sequences and annotation. The website thereof is: http://www.mirbase.org/. See also Griffiths-Jones S, et al., "miRBase: tools for microRNA genomics. NAR 2008 36 (Database Issue): D154-D158; Griffiths-Jones S, et al. "miRBase: microRNA sequences, targets and gene nomenclature." NAR 2006 34(Database Issue): D140-D144 or Griffiths-Jones S., "The microRNA Registry.", NAR 2004 32(Database Issue): D109-D111.

The above indicated sequences are also contained in the attached sequence listing as SEQ ID NO: 1 to 121 with SEQ ID NO: 1 being hsa-mir-371, SEQ ID NO: 2 being hsa-miR-371-3p etc.

The level of at least one miR can be measured in cells of a biological sample obtained from the subject. For example, a tissue sample can be removed from a subject suspected of having tumor associated with a chromosomal rearrangement by conventional biopsy techniques. Such tissue sample may form a or the test sample. In another example, a blood sample can be removed from the subject, and white blood cells can be isolated for DNA extraction by standard techniques which preferably forms a or the test sample. The blood or tissue sample is preferably obtained from the subject prior to initiation of radiotherapy, chemotherapy or other therapeutic treatment. A control sample which may also be referred to as a or the normal sample, such as a corresponding control tissue or blood sample can be obtained from unaffected tissues of the subject, from a normal human individual or population of normal individuals, or from cultured cells corresponding to the majority of cells in the subject's sample. The control sample such as a or the corresponding tissue or blood sample is then processed along with the sample from the subject, so that the levels of miR produced from a given miR gene in cells from the subject's sample can be compared to the corresponding miR levels from cells of the control sample. This procedure is applicable to each and any method, process or use disclosed herein where a test sample, normal sample or control sample is used.

An alteration, i.e. an increase in the level of a miR in the sample obtained from the subject, relative to the level of a corresponding miR in a control sample, is indicative of the presence of tumor in the subject. In accordance with the present invention, the level of the at least one miR in the test sample is greater than the level of the corresponding miR in the control sample (i.e., expression of the miR is "up-regulated"). As used herein, expression of a miR is "up-regulated" when the amount of miR in a cell or tissue sample from a subject is greater than the amount of the same miR in a control cell or control tissue sample. The relative miR gene expression in the control and normal samples can be determined with respect to one or more RNA expression standards. The standards can comprise, for example, a zero miR gene expression level, the miR gene expression level in a standard cell line, or the average level of miR gene expression previously obtained for a population of normal human controls. This is applicable to each and any method, process or use disclosed herein.

The level of a miR in a sample can be measured using any technique that is suitable for detecting RNA expression levels in a biological sample. Suitable techniques for determining RNA expression levels in cells from a biological sample (e.g., Northern blot analysis, RT-PCR, in situ hybridization) are well known to those of skill in the art; see also the Examples. In a particular embodiment, the level of at least one miR is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question; see, for example, Molecular Cloning: A Laboratory Manual, J. Sambrook et al., eds., 2nd edition, Cold Spring Harbor Laboratory Press, 1989, Chapter 7, the entire disclosure of which is incorporated by reference. This is applicable to each and any method, process or use disclosed herein.

Suitable probes for Northern blot hybridization of a given miR can be produced from the nucleic acid sequences of the given miR. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^3H$, $^{32}P$, $^{33}P$, $^{14}C$, or $^{35}S$; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al., J. Mol. Biol. 113 (1977), 237-251 or by the random priming method of Feinberg et al., Anal. Biochem. 132 (1983), 6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram.

Autoradiographic detection of hybridization can then be performed by exposing hybridized filters to photographic film. Densitometric scanning of the photographic filmsexposed by the hybridized filters provides an accurate measurement of miR gene transcript levels. Using another approach, miR gene transcript levels can be quantified by computerized imaging systems, such the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR can be produced from the nucleic acid sequences. This in situ hybridization is applicable to each and any method, process or use disclosed herein.

In connection with each and any method, process or use disclosed herein the relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., 5S rRNA, U6 snRNA or tRNAs. The methods for quantitative RT-PCR and variations thereof are within the skill in the art.

In some instances of the methods, processes or uses disclosed herein, it may be desirable to simultaneously determine the expression level of a plurality of different miRs in a sample. In other instances of such methods, processes or uses disclosed herein, it may be desirable to determine the expression level of the transcripts of all known miR genes correlated with a tumor. Assessing tumor-specific expression levels for hundreds of miR genes is time consuming and requires a large amount of total RNA (at least 20 pg for each Northern blot) and autoradiographic techniques that require radioactive isotopes.

To overcome these limitations, an oligolibrary, in microchip format (i.e., a microarray), may be constructed containing a set of probe oligodeoxynucleotides that are specific for a set of miR genes. Using such a microarray, the expression level of multiple microRNAs in a biological sample can be determined by reverse transcribing the RNAs to generate a set of target oligodeoxynucleotides, and hybridizing them to probe oligodeoxynucleotides on the microarray to generate a hybridization, or expression, profile. The hybridization profile of the test sample can then be compared to that of a control sample to determine which microRNAs have an altered expression level in tumor. This is applicable to each and any method, process or use disclosed herein.

As used herein, "probe oligonucleotide" or "probe oligodeoxynucleotide" refers to an oligonucleotide that is capable of hybridizing to a target oligonucleotide.

"Target oligonucleotide" or "target oligodeoxynucleotide" refers to a molecule to be detected (e.g., via hybridization).

By "miR-specific probe oligonucleotide" or "probe oligonucleotide specific for an miR" is meant a probe oligonucleotide that has a sequence selected to hybridize to a specific miR, or to a reverse transcript of the specific miR.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal cells may be distinguished from tumor cells, and within tumor cells, different prognosis states (good or poor long term survival prospects, for example) may be determined. By comparing expression profiles of tumor cells in different states, information regarding which genes are important (including both up- and down-regulation of genes) in each of these states is obtained.

As preferably used herein, the term "chromosomal rearrangement" shall mean in an embodiment the non-homologuous rearrangement of parts of one or several chromosomes which may, for example, be effected by chromosomal translocation, inversion or interstitial deletions.

A chromosomal rearrangement is preferably detected by means of classic cytogenetics or molecular cytogenetics including but not limited to in situ hybridisation.

As preferably used herein, the term that a tumor involves a chromosomal rearrangement shall mean in an embodiment that the at least some of the tumor cells show or exhibit such chromosomal rearrangement.

As preferably used herein, the term that a result is "indicative" of a subject, e.g., having a tumor shall mean that the result provides evidence that the subject has a tumor.

The identification of sequences that are differentially expressed in tumor cells or normal cells, as well as differential expression resulting in different prognostic outcomes, allows the use of this information in a number of ways. For example, a particular treatment regime may be evaluated (e.g., to determine whether a chemotherapeutic drug act to improve the long-term prognosis in a particular patient).

Similarly, diagnosis may be done or confirmed by comparing patient samples with the known expression profiles. Furthermore, these gene expression profiles (or individual genes) allow screening of drug candidates that suppress the tumor expression profile or convert a poor prognosis profile to a better prognosis profile.

Accordingly, the invention provides methods of diagnosing whether a subject has, or is at risk for developing, a tumor as defined herein, comprising reverse transcribing RNA from a test sample obtained from the subject to provide a set of target oligo-deoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample, wherein an alteration, in particular increase in the signal of at least one miRNA is indicative of the subject either having, or being at risk for developing, tumor.

In one embodiment, the microarray comprises miRNA-specific probe oligonucleotides for a substantial portion of the C19MC and miR-371-3 cluster.

The microarray can be prepared from gene-specific oligonucleotide probes generated from known miRNA sequences.

The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmiGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/ 30% formamide at 25° C. for 18 hours, followed by washing in 0.75×TNT at 37° C. for 40 minutes.

At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labelled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 pg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the members of the C19MC and miR-371-3 cluster, preferably the entire miRNome thereof, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having tumor is quantitatively reverse transcribed to provide a set of labelled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, i.e., nontumorous, control sample. An alteration in the signal is indicative of the presence of the tumor in the subject.

The above disclosure as to the use of a compound capable of inhibiting expression of at least one miR as defined and, respectively, disclosed herein, for treating a subject suffering from a tumor equally apply for the treatment of a subject suffering from or being at risk of suffering from a placenta and/or pregnancy disorders as disclosed herein. The same applies to the respective pharmaceutical compositions.

Other techniques for measuring miR gene expression are also within the skill in the art, and include various techniques for measuring rates of RNA transcription and degradation.

The terms "treat", "treating" and "treatment", as used herein, refer to ameliorating symptoms associated with a disease or condition, for example, tumor, including preventing or delaying the onset of the disease symptoms, and/or lessening the severity or frequency of symptoms of the disease or condition. The terms "subject" and "individual" are defined herein to include animals, such as mammals, including but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

In one embodiment of the treatment methods of the invention, an effective amount of at least one compound which inhibits miR expression can be administered to the subject. As used herein, "inhibiting miR expression" means that the production of the active, mature form of miR after treatment is less than the amount produced prior to treatment. One skilled in the art can readily determine whether miR expression has been inhibited in a tumor cell, using for example the techniques for determining miR transcript level discussed above for the diagnostic method. Inhibition can occur at the level of gene expression (i.e., by inhibiting transcription of a miR gene encoding the miR) or at the level of processing (e.g., by inhibiting processing of a miR precursor into a mature, active miR).

As used herein, an "effective amount" of a compound that inhibits miR expression is an amount sufficient to inhibit proliferation of a tumor cell in a subject suffering from a tumor associated with a tumor-associated chromosomal feature. One skilled in the art can readily determine an effective amount of an miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate or estimated body weight of a subject to be treated. Such effective amounts are administered parenterally or enterally, among others, as described herein. For example, an effective amount of the expression-inhibiting compound administered to a subject can range from about 5-3000 micrograms/kg of body weight, from about 700-1000 micrograms/kg of body weight, or it can be greater than about 1000 micrograms/kg of body weight.

One skilled in the art can also readily determine an appropriate dosage regimen for administering a compound that inhibits miR expression to a given subject. For example, an expression-inhibiting compound can be administered to the subject once (e.g., as a single injection or deposition). Alternatively, an expression-inhibiting compound can be administered once or twice daily to a subject for a period of from about three to about twenty-eight days, more preferably from about seven to about ten days. In a particular dosage regimen, an expression-inhibiting compound is administered once a day for seven days. Where a dosage regimen comprises multiple administrations, it is understood that the effective amount of the expression-inhibiting compound administered to the subject can comprise the total amount of compound administered over the entire dosage regimen.

Suitable compounds for inhibiting miR gene expression include doublestranded RNA (such as short- or small-interfering RNA or "siRNAn), antisense nucleic acids, and enzymatic RNA molecules, such as ribozymes. Each of these compounds can be targeted to a given miR and destroy or induce the destruction of the target miR.

For example, expression of a given miR gene can be inhibited by inducing RNA interference of the miR gene with an isolated double-stranded RNA ("dsRNA") molecule which has at least 90%, for example at least 95%, at least 98%, at least 99% or 100%, sequence homology with at least a portion of the miR. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick basepairing interactions (hereinafter "base-paired"). The sense strand comprises a nucleic acid sequence which is substantially identical to a nucleic acid sequence contained within the target miR.

As used herein, a nucleic acid sequence in an siRNA which is "substantially identical" to a target sequence contained within the target mRNA is a nucleic acid sequence that is identical to the target sequence, or that differs from the target sequence by one, two or more nucleotides provided that such an siRNA molecule is still suitable to mediate RNA interference. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described for isolated miRs in international application WO 2009/033140, the disclosure content of which is incorporated herein by reference in its entirety. Exemplary methods for producing and testing dsRNA or siRNA molecules are described in US published patent application No. 2002/0173478 A1 and in US published patent application No. 2004/0018176 A1, the entire disclosures of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in an miR. The antisense nucleic acid can comprise a nucleic acid sequence that is 50-100% complementary, 75-100% complementary, or 95-100% complementary to a contiguous nucleic acid sequence in an miR. Nucleic acid sequences for the miRs are provided herein. Without wishing to be bound by any theory, it is believed that the antisense nucleic acids activate RNase H or another cellular nuclease that digests the miR/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described for the isolated miRs. Exemplary methods for producing and testing are within the skill in the art; see, e.g., Stein and Cheng, Science 261 (1993), 1004 and U.S. Pat. No. 5,849,902, the entire disclosures of which are incorporated herein by reference.

More recently, chemically modified antisense oligonucleotides (ASOs) are used as a tool to functionalize microRNAs (miRNAs) and reduction of miRNA level after ASO inhibition is commonly reported to show efficacy. For example, inhibition of miRNA expression by 2'-o-methyl oligonucleotides in *Drosophila* S2 cells has been described by Berger et al, in In Vitro Cell Dev. Biol. Anim. 41 (2005), 12-18. In addition, potent inhibitors of microRNA based on ASOs in vivo without degradation have described in Davies et al., Nucleic Acids Res. 37 (2009), 70-77, the disclosure content of both documents being incorporated by reference herein. A similar approach may be used in accordance with the present invention in order inhibit expression and activity, respectively, of the miRNAs associated with the chromosomal rearrangement such as those of the miR-371-3 and C19MC cluster.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of an miR, and which is able to specifically cleave the miR. The enzymatic nucleic acid substrate binding region can be, for example, 50-100% complementary, 75-100% complementary, or 95-100% complementary to a contiguous nucleic acid sequence in an miR. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described for the isolated miRs. Exemplary methods for producing and testing enzymatic nucleic acid molecules, i.e. ribozymes are described in Werner and Uhlenbeck, Nucl. Acids Res. 23 (1995), 2092-2096; Hammann et al., Antisense and Nucleic Acid Drug Dev. 9 (1999), 25-31; Steinecke et al., EMBO J. 11 (1992), 1525-1530; Steinecke et al., Gene 149 (1994), 47-54, and U.S. Pat. No. 4,987,071, the entire disclosures of which are incorporated herein by reference.

Another group of compounds for inhibiting miR gene expression are the so-called antagomiRs as described, for example, by Krützfeldt J et al. (Krützfeldt J et al., (2005) Silencing of microRNAs in vivo with 'antagomirs'. Nature 438 (7068): 685-689.)

Administration of at least one compound for inhibiting miR expression, will inhibit the proliferation of tumor cells in a subject who has a tumor associated with a tumor-associated chromosomal feature. As used herein, to "inhibit the proliferation of a tumor cell" means to kill the cell, or permanently or temporarily arrest or slow the growth of the cell. Inhibition of tumor cell proliferation can be inferred if the number of such cells in the subject remains constant or decreases after administration of the miR gene expression-inhibiting compounds. An inhibition of tumor cell proliferation can also be inferred if the absolute number of such cells increases, but the rate of tumor growth decreases.

The number of tumor cells in a subject's body can be determined by direct measurement, or by estimation from the size of primary or metastatic tumor masses. For example, the number of tumor cells in a subject can be measured by immunohistological methods, flow cytometry, or other techniques designed to detect characteristic surface markers of tumor cells.

The miR gene expression-inhibiting compounds can be administered to a subject by any means suitable for delivering these compounds to tumor cells of the subject. For example, the miR expression inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene expression inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N[1-(2,3-dioleoyloxy)propyl]-N,N,N-triyl-ammonimumet methylsulfate, Roche Diagnostics GmbH, Roche Applied Science, Nonnenwald 2, 82372 Penzberg, Germany or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

An miR gene expression inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and intravenous administration into the patient.

In the present methods, an miR expression inhibiting compound can be administered to the subject either as naked RNA, in combination with a delivery reagent, or as a nucleic acid (e.g., a recombinant plasmid or viral vector) comprising sequences that express the miR expression inhibiting compound. Suitable delivery reagents include, e.g., the Mirus Transit TKO lipophilic reagent; lipofectin; lipofectamine; cellfectin; polycations (e.g., polylysine), and liposomes.

Recombinant plasmids and viral vectors comprising sequences that express the miR gene expression inhibiting compounds, and techniques for delivering such plasmids and vectors to tumor cells, are discussed herein.

In a particular embodiment, liposomes are used to deliver an miR gene expression-inhibiting compound (or nucleic acids comprising sequences encoding them) to a subject. Liposomes can also increase the blood half-life of the nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al., Ann. Rev. Biophys. Bioeng. 9 (1980), 467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to tumor cells. Ligands which bind to receptors prevalent in tumor cells, such as monoclonal antibodies that bind to tumor cell antigens, are preferred.

The liposomes for use in the present methods can also be modified so as to avoid clearance by the mononuclear macrophage system ("MMS") and reticulo endothelial system ("RES"). Such modified liposomes have opsonization-inhibition moieties on the surface or incorporated into the liposome structure. In a particularly preferred embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonisation inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes; see Gabizon, et al., Proc. Natl. Acad. Sci., U.S.A., 18 (1988), 6949-6953. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene expression inhibition compounds (or nucleic acids comprising sequences encoding them) to tumor cells.

The miR gene expression inhibition compounds can be formulated as pharmaceutical compositions, sometimes called "medicaments," prior to administering them to a subject, according to techniques known in the art. Accordingly, the invention encompasses pharmaceutical compositions for treating tumor. In one embodiment, the pharmaceutical compositions comprise at least one isolated miR expression inhibition compound. In a particular embodiment, the at least one miR gene expression inhibition compound is specific for a miR gene whose expression is greater in tumor cells than control cells.

Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985) and update version Remington: The Science and Practice of Pharmacy (2000) by the University of Sciences in Philadelphia, ISBN 0-683-306472, the entire disclosure of both documents which is incorporated herein by reference.

The present pharmaceutical formulations comprise at least one miR gene expression inhibition compound (or at least one nucleic acid comprising sequences encoding them) (e.g., 0.1 to 90% by weight), or a physiologically acceptable salt thereof, mixed with a pharmaceutically-acceptable carrier. The pharmaceutical formulations of the invention can also comprise at least one miR gene expression inhibition compound (or at least one nucleic acid comprising sequences encoding them) which are encapsulated by liposomes and a pharmaceutically-acceptable carrier.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene expression inhibition compound (or at least one nucleic acid comprising sequences encoding them) which is resistant to degradation by nucleases. One skilled in the art can readily synthesize nucleic acids which are nuclease resistant, for example by incorporating one or more ribonucleotides that are modified at the 2'-position into the miRs. Suitable 2'-modified ribonucleotides include those modified at the 2'-position with fluoro, amino, alkyl, alkoxy, and 0-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene expression inhibition compound (or at least one nucleic acid comprising sequences encoding them). A pharmaceutical composition for aerosol (inhalational) administration can comprise 0.01-20% by weight, preferably 1%-10% by weight, of the at least one miR gene expression inhibition compound (or at least one nucleic acid comprising sequences encoding them) encapsulated in a liposome as described above, and a propellant. A carrier can also be included as desired; e.g., lecithin for intranasal delivery.

The invention also encompasses methods of identifying an anti-tumor agent, comprising providing a test agent to a cell and measuring the level of at least one miR in the cell. In one embodiment, the method comprises providing a test agent to a cell and measuring the level of at least one miR associated with increased expression levels in tumor cells. A decrease in the level of the miR in the cell, relative to a suitable control cell, is indicative of the test agent being an anti-tumor agent.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR (e.g., Northern blotting, in situ hybridization, RT-PCR, expression profiling) are also well known in the art.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003). The practice of the present invention will employ, unless otherwise indicated, conventional techniques of cell biology, cell culture, molecular biology, transgenic biology, microbiology, recombinant DNA, and immunology, which are within the skill of the art.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11 (2001), 98-107.

Supplementary Material and Methods

Detailed descriptions of conventional methods, such as those employed herein can be found in the cited literature.

Tissue and Cell Lines

All samples were obtained from patients undergoing thyroid resection in the Department of General and Visceral Surgery of the St. Joseph Stift, Bremen (Germany). Approval for the project was obtained was from the local ethics committee and followed the principles for medical research involving human subjects outlined in the Helsinki declaration (paragraph 25). One piece of each tumor was stored in Hank's solution for cell culture and a second piece was stored in liquid nitrogen for gene expression studies. The cell lines were derived from thyroid adenoma cells as reported previously (Belge et al., J. Cell Biol. Int. Rep. 16, (1992) 339-347). Archival RNAs from fetal, placental and testicular tissue were used as controls.

Cell Culture and Cytogenetic Analyses

Tissue digestion, cultivation of primary cell lines, and cytogenetic analyses were performed according to previously described methods (Belge et al., Cancer Genet. Cytogenet. 101 (1998), 42-48; Roque et al., Cancer Genet. Cytogenet. 67 (1993), 1-6). Before digestion, each sample was touched onto slides to get samples for FISH screening.

Isolation of RNA, reverse transcription and real-time PCR (qRT-PCR) quantification Total RNA was extracted from tissue as well as from immortalized cell lines using Trizol (Invitrogen, Karlsruhe, Germany) reagent, or mirVana (Ambion, Woodward, USA) miRNA isolation kit according to the manufacturer's instructions. miRNA (miR-371-3p, miR-372, miR-373 and miR-520c) and RNU6B (RNA, U6 small nuclear 2; internal control for relative quantification)-specific cDNA were generated from 10 ng of total RNA using the TaqMan microRNA RT Kit and the gene-specific RT primers from the TaqMan microRNA Assays (Applied Biosystems, Foster City, Calif., USA) according to the manufacturer's instructions. The reactions were incubated in a thermal cycler for 30 min at 16° C., 30 min at 42° C., 5 min at 85° C. and then stored at 4° C. All reverse transcriptions included no-template controls and minus RT controls (-RT). Real-time PCR was performed using an Applied Biosystems 7300 Fast Real Time PCR system with miRNA and RNU6B-specific probes and TaqMan Universal PCR Master Mix (Applied Biosystems, Foster City, Calif., USA). The reactions were incubated in 96-well plates at 95° C. for 10 min followed by 40 cycles of 15 s at 95° C. and one min at 60° C. All reactions were run in triplicate. Relative quantification (RQ) was calculated using Applied Biosystems SDS software based on the RQ=2_DDCt 2(-Delta Delta C(T)) method (Livak et al., Methods 25 (2001), 402-408). Ct data were normalized to the internal control, RNU6B (Yu et al., Cancer Cell 13 (2008), 48-57).

Detection of Fusion Transcripts Via 3'RACE-PCR

3'RACE-PCR were performed on cell line S40.2. Total RNA was isolated using RNeasy Mini Kit (Qiagen, Hilden, Germany). cDNA syntheses were carried out with slight modifications following the instructions for the M-MLV reverse transcriptase using oligo(dT) primer as anchor primer (Invitrogen, Karlsruhe, Germany). 3'RACE-PCRs and Nested 3'RACE-PCRs were performed as described in the Gene Racer Kit (Invitrogen, Karlsruhe, Germany) adjusted to the conditions for GoTaq Flexi DNA Polymerase (Promega, Mannheim, Germany). Southern Blots was carried out as mentioned by Fehr et al. (Fehr et al., J. Cancer Genet. Cytogenet. 180 (2008), 135-139) with a PUM/-specific probe labelled with digoxigenin-11-dUTP (RocheDiagnostics, Penzberg, Germany). Fragments of interest were excised and extracted with the QIAquick Gel Extraction Kit (Qiagen, Hilden, Germany) and were then cloned into the pGEM-T Easy Vector (Promega, Mannheim, Germany). The plasmid DNA from the clones of interest was isolated via QIAprep Spin Miniprep Kit (Qiagen, Hilden, Germany) and sequenced by Eurofins MWG, Ebersberg, Germany.

Primers for Detection of Fusion Transcripts Via 3' RACE-PCR pum1-specific Primers (Primer (Exon) Sequence (5'-3')):

```
Ex1_Up (Exon 2)      CCCTCAAGAACCAGCTAATCCCAACA
                     (SEQ ID NO: 122)

Ex3_Up (Exon 4)      TTCCTGGGTGATCAATGGCGAGA
                     (SEQ ID NO: 123)

Ex4_Up (Exon 5)      TCCCCGGGCGATTCCTGTCT
                     (SEQ ID NO: 124)

Ex5_Lo (Exon 6)      TCCATCACATCACCCTCCTCCTTCAA
                     (SEQ ID NO: 125)

Ex7_Up (Exon 8)      ACCTAATGCGCTTGCTGTCCA
                     (SEQ ID NO: 126)

Ex8_Up (Exon 9)      GCTCCCGCTGCGTTTGTCC
                     (SEQ ID NO: 127)

Ex9_Up (Exon 10)     CAACAGACCACCCCACAGGCTCAG
                     (SEQ ID NO: 128)
```

Primer for cDNA-Synthesis (Primer Sequence (5'-3')):

```
AP2
AAGGATCCGTCGACATC(T)17
(SEQ ID NO: 129)

Oligo dT
GCTGTCAACGATACGCTACGTAACGGCATGACAGTG(T)24
(SEQ ID NO: 130)
```

Primers for 3'RACE-PCR (Primer Sequenz (5'-3')):

```
UAP2              CTACTACTACTAAAGGATCCGTCGACATC
                  (SEQ ID NO: 131)

Gene Racer 3'     GCTGTCAACGATACGCTACGTAACG
                  (SEQ ID NO: 132)

Gene Racer 3'     CGCTACGTAACGGCATGACAGTG
Nested            (SEQ ID NO: 133)
```

PUM1-specific probes for Souther-blot, generated by PCR:
1. Seq. between primers Ex4_Up and Ex5_Lo
2. Seq. between primers Ex3_Up und Ex5_Lo Primers:

```
Ex3_Up (Exon 4) =     TTCCTGGGTGATCAATGGCGAGA
                      (SEQ ID NO: 134)
Ex4_Up (Exon 5) =     TCCCCGGGCGATTCCTGTCT
                      (SEQ ID NO: 135)
Ex5_Lo (Exon 6) =     TCCATCACATCACCCTCCTCCTTCAA
                      (SEQ ID NO: 136)
```

Detection of Fusion Transcripts Via RT-PCR

With the program polyadq (Tabaska et al., Gene 231 (1999), 77-86), the possible PolyA-site of the C19MC-cluster was detected. Nearby a primer was designed which was later used together with a PUM1-specific primer. Total RNA of S40.2 was isolated via TRIzol reagent (Invitrogen, Karlsruhe, Germany) used for cDNA syntheses as previously described. PCR was done with the GoTaq Flexi DNAPolymerase (Promega, Mannheim, Germany) followed by a semi-nested PCR. Fragments of interest were excised and extracted as described above and sequenced by Eurofins MWG, Ebersberg, Germany.

Primers for Detection of the Fusion Transcript Via RT-PCR

```
pum1-Primer: Ex8_Up
GCTCCCGCTGCGTTTGTCC
(SEQ ID NO: 137)

pum1-Primer: Ex9_Up
CAACAGACCACCCCACAGGCTCAG
(SEQ ID NO: 138)

#19-Primer: 500-Cluster_PolyA_I
CAACCGTTGGGGATTACAAAATAGA
(SEQ ID NO: 139)
```

Validation of the Fusion Transcript

The former results were confirmed by using different primers localized within the fusion transcript. The PCRs were carried out as described above. Fragments of the expected size were excised, extracted and sequenced (see above).

Primers for Validation of the Fusion Transcript

```
#19-Primer: 19_1      GGCTGCCCAGGGAGTTGCT
                      (SEQ ID NO: 140)
```

```
#19-Primer: 19_2      GCAGAAGCTCCCAGCCAGATCTT
                      (SEQ ID NO: 141)

#19-Primer: 19_3      CTAGGGTTCGCTGTCCTCACACTGC
                      (SEQ ID NO: 142)

pum1-Primer: Ex8_Up   GCTCCCGCTGCGTTTGTCC
                      (SEQ ID NO: 143)

pum1-Primer: Ex9_Up   CAACAGACCACCCCACAGGCTCAG
                      (SEQ ID NO: 144)
```

RT-PCR miRNA-specific-primers for miR-512-5p, miR-517a and miR-519a were designed as described by Chen et al. (Chen et al., Nucleic Acids Res. 33 (2005), e179). cDNA was generated from 1 pg total RNA according to Chen et al. (2005), supra, with small modifications in stem-loop-primer concentration (5 nM), as well as the PCR reactions that were modified in annealing-temperature (68° C.) and -duration (10 s). RT-PCR was performed with GoTaq Flexi DNA-Polymerase (Promega GmbH, Mannheim, Germany). Elongation was run at 72° C. for 15 s.

miRNA-Specific-Primers

```
miR-371-5p loop primer (SEQ ID NO: 145):
GTCGTATCCAGTGCAGGGTCCGAGGTATTCGCACTGGATACGACACAC
TC miR-371-5p loop primer (SEQ ID NO: 146):
GTCGTATCCAGTGCAGGGTCCGAGGTATTCGCACTGGATACGACAGTG
CC miR-372 loop primer (SEQ ID NO: 147):
GTCGTATCCAGTGCAGGGTCCGAGGTATTCGCACTGGATACGACACGC
TC miR-373 loop primer (SEQ ID NO: 148):
GTCGTATCCAGTGCAGGGTCCGAGGTATTCGCACTGGATACGACACAC
CC miR-512-5p loop primer (SEQ ID NO: 149):
GTCGTATCCAGTGCAGGGTCCGAGGTATTCGCACTGGATACGACGAAA
GT miR-517a loop primer (SEQ ID NO: 150):
GTCGTATCCAGTGCAGGGTCCGAGGTATTCGCACTGGATACGACACAC
TC miR-520c-3p loop primer (SEQ ID NO: 151):
GTCGTATCCAGTGCAGGGTCCGAGGTATTCGCACTGGATACGACACCC
TC miR-520c-5p loop primer (SEQ ID NO: 152):
GTCGTATCCAGTGCAGGGTCCGAGGTATTCGCACTGGATACGACCAGA
AA miR-371-3p forward
ACCGCTAAGTGCCGCCATCTTTTG
(SEQ ID NO: 153)

miR-371-5p forward
GCCGCCACTCAAACTGTGGGG
(SEQ ID NO: 154)

miR-372 forward
GGTCATAAAGTGCTGCGACATTTG
(SEQ ID NO: 155)

miR-373 forward
TTCATGAAGTGCTTCGATTTTGG
(SEQ ID NO: 156)

miR-512-5p forward
AGTCTACACTCAGCCTTGAGGGCA
(SEQ ID NO: 157)

miR-517a forward
CGGCGGATCGTGCATCCCTTTA
(SEQ ID NO: 158)

miR-519a forward
CCGGCTAAAGTGCATCCTTTTAG
(SEQ ID NO: 159)

miR-520c-3p forward
GCCGCCAAAGTGCTTCCTTTTAG
(SEQ ID NO: 160)

miR-520c-5p forward
ACCGCTCTCTAGAGGGAAGCAC
(SEQ ID NO: 161)

Reverse Primer
GTGCAGGGTCCGAGGT
(SEQ ID NO: 162)
```

Fluorescence In Situ Hybridization (FISH)

I-FISH analyses were performed on touch-preparations of thyroid tumors. For detection of 19q13.4 rearrangements a dual-color, break-apart rearrangement probe (PanPath, Budel, Netherlands) referred to as tbpc19 (thyroid breakpoint cluster 19q13) was used. The rearrangement probe is a mixture of two probes located distal (3'-tbpc19; labelled by Alexa Fluor 488) and proximal (5'-tbpc19; labelled by AlexaFluor 555), respectively, of the common breakpoint-cluster region in 19q13.4 in benign thyroid lesions. 10 µl of the break-apart probe were used per slide. Co-denaturation was performed on a Mastercycler gradient (Eppendorf, Hamburg, Germany) for 3 min at 80° C. followed by overnight hybridization in a humidified chamber at 37° C. Post-hybridization was performed at 61° C. for 5 min in 0.1×SSC. Interphase nuclei were counterstained with DAPI (0.75 µg/ml). Slides were examined with a Axioskop 2 plus fluorescence microscope (Carl Zeiss, Gottingen, Germany). Images were captured with an AxioCam MRm digital camera and were edited with Axio-Vision (Carl Zeiss, Gottingen, Germany). For each case 200 non-overlapping nuclei were scored. Co-localized signals (green/red) indicate a non-rearranged breakpoint region, whereas separated green and red signals indicate a rearrangement of the chromosomal region 19q13.4. Metaphase-FISH with tbpc-19 on case 5842 was performed as described above for I-FISH on touch preparations. Treatment of metaphases was carried out as described by Kievits et al. (Kievits et al., Cytometry 11 (1990), 105-109). For determination of the breakpoint on chromosome 1 FISH was performed on metaphase preparations of the cell line S40.2. As probes two overlapping clones RP11-1136E4 (AQ707626 and AQ733864) and RP11-201O14 (AL356320.8) (imaGenes, Berlin, Germany) both spanning the whole genomic sequence of PUM1 were used. DNA was isolated using Qiagen Plasmid Midi Kit (Qiagen, Hilden, Germany). 1 µg of isolated plasmid DNA was labelled by nick translation (Roche, Mannheim, Germany) either with digoxigenin-11-dUTP (RP11-201O14) or biotin-16-dUTP (RP11-1136E4). Treatment of metaphases and subsequent FISH experiments were carried out as described previously by Kievits et al. (1990), supra, with exception for co-denaturation and post-hybridization which were performed as described above.

Chromosome 19 Probes:

| Lokalisation | name | Clon | Accession-Nr. |
|---|---|---|---|
| 19q13, distal of breakpoint | 3'-tbpc19 | CTD-3022G6 (BC829651) RP11-158G19 | AC008753 (CTD-3022G6) AC022318 |
| 19q13, proximal of breakpoint | 5'-tbpc19 | PAC13173 | no |

PAC13173 corresponds to the BAC-clones AC011453.4 and AC011487.5

Statistical Analysis

Results are presented as the mean±standard error (SE). Statistical comparisons were performed by a nonpaired Student's t-test. A p-value of less than 0.05 was considered significant.

Example 1

In Silico Analyses Reveals the Close Proximity of C19MC and miR-371-3 to the 19q13.4-Breakpoint Cluster in Thyroid Tumors About 20% of the thyroid tumors with clonal cytogenetic aberrations show abnormalities involving chromosomal band 19q13 (Beige, G. et al. Cancer Genet. Cytogenet. 101 (1998) 42-48). So far, by positional cloning and in silico analyses the breakpoints have been found to cluster within a segment of 150 kb (kilobases) (Beige et al., Cytogenet. Cell Genet. 93, (2001), 48-51) that is located in close proximity to the genes encoding two miRNA clusters, i.e. C19MC and miR-371-3 (FIG. 4). The 100 kb long C19MC cluster with 46 tandemly repeated, primate-specific miRNA genes accounts for about 8% of all known human miRNA genes making it the largest human miRNA gene cluster discovered to date (Bortolin-Cavaille et al., Nucleic Acids Res. 37 (2009), 3464-3473). Ren et al. (Ren et al., J. Transl. Med. 7 (2009), 20) have predicted 4,691 targets for this cluster. Recent evidence suggests that its miRNAs are encoded by an intron of a non-protein coding Pol-II transcript which is mainly expressed in the placenta (Bortolin-Cavaille et al. (2009), supra). In contrast to that large cluster the miR-371-3 cluster is much smaller spanning a region of approximately 1,050 bp where five miRNAs are encoded. The miRNAs of both clusters belong to a large miRNA family sharing a similar seed sequence (Laurent et al., Stem Cells 26 (2008), 1506-1516). Of note, several groups recently have linked the expression of members of the C19MC as well as the miR-371-3 cluster with the miRNA signature characteristic for human embryonic stem cells (hESC) (Ren et al. (2009), supra; Laurent et al. (2008), supra; Li et al., J. Cell. Biochem. 106 (2009), 1020-1030). First evidence for an oncogenic potential of miR-373 has been obtained in human testicular germ cell tumors where it was shown to allow tumorigenic growth in the presence of wild-type p53 (Voorhoeve et al., Cell 124 (2006), 1169-1181). In prostate tumor both miR-373 and miR-520c although found to be down-regulated stimulated migration and invasion in vitro (Yang et al., Int. J. Clin. Exp. Pathol. 2 (2009), 361-369). Recently, Huang et al. (Huang et al., Nat. Cell Biol. 10 (2008), 202-210) were able to demonstrate that miR-373 and miR-520c promote tumor invasion and metastasis in vivo and in vitro by the suppression of CD44. Interestingly, qualitative and quantitative changes of CD44 expression have been implicated in the growth and progression of thyroid tumors. Because invasive behavior is of pivotal significance in the differential diagnosis of thyroid tumors experiments were performed to address the question on a possible up-regulation of both miRNA clusters in thyroid adenomas.

Example 2

Adenomas with 19q13 Aberrations Express Significantly Higher Levels of Members of the C19MC Cluster than Those without that Translocation To evaluate the role of either of these two clusters as a possible target of the 19q13 translocations in thyroid adenomas, RT-PCR was used to compare the expression of three members of the C19MC cluster, i.e. miR-512-5p, miR-517a, and miR-519a in five cell lines established from thyroid adenomas with 19q13 rearrangements and three cell lines from adenomas with other clonal abnormalities; see Table 2.

TABLE 2

Used tissue samples and cell lines.

| sample no. | thyroid material | cytogenetic subtype/ FISH karyotype |
|---|---|---|
| S40.2 | cell line | 46, XX, t(1; 19)(p35 or p36; q13)[19] |
| S121 | cell line | 46, XX, t(5; 19)(q13; q13)[52] |
| S141.2 | cell line | 46, XX, t(2; 19)(p12 or p13; q13)[59] |
| S211 | cell line | 46, XX, inv(4)(p15.2q12), t(5; 19)(p14 or 15.1; q13), t(9; 18)(q12; q22)[25] |
| S270.2 | cell line | 46, XX, t(2; 3)(q21; q27 or q28)[13] |
| S290.1 | cell line | 46, XX, t(11; 19)(q23; q13)[19] |
| S325 | cell line | 46, XX, t(2; 20; 3)(p21; q11.2; p25)[17] |
| S533 | cell line | 46, XX, t(2; 7)(p21; p15)[16] |
| S805 | adenoma | 46, XX |
| S806 | adenoma | 46, XX |
| S889 | adenoma | 46, XX |
| S920 | adenoma | 46, XX |
| S925 | adenoma | 46, XX |
| S801 | adenoma | 46, XY, t(2; 4), t(2; 14; 19) nuc ish(5'-tbpc19, 3'-tbpc19) × 2(5'-tbpc19 sep 3'-tbpc19 × 1) |
| S814 | adenoma | 46, XX, del(6)(q21~22) nuc ish(5'-tbpc19, 3'-tbpc19) × 2(5'-tbpc19 sep 3'-tbpc19 × 1) |
| S842 | adenoma | 46, XX, t(1; 19)(q32; q13)[8]/46, XX[24] nuc ish(5'-tbpc19, 3'-tbpc19) × 2(5'-tbpc19 sep 3'-tbpc19 × 1) |
| S846 | adenoma | 46, XY nuc ish(5'-tbpc19, 3'-tbpc19) × 2(5'-tbpc19 sep 3'-tbpc19 × 1) |
| S849 | adenoma | not evaluable by cc nuc ish(5'-tbpc19, 3'-tbpc19) × 2(5'-tbpc19 sep 3'-tbpc19 × 1) |

Cytogenetic details of the analyzed samples from follicular thyroid tumors and the cell lines used with their genetic subgroups determined by conventional cytogenetics and/or by interphase fluorescence in situ hybridization (1-FISH) with break-apart, dual-color rearrangement probe (tbpc-19). In case of the cell lines only the clonal aberrations found in the original tumors the cell lines have been established from are given.

All cell lines had been established from primary tumors by using a SV40 derived subgenomic fragment. Four of the five cell lines with 19q13 rearrangements expressed detectable levels of the three miRNAs whereas in the remaining cell line (S121, Table 2) and all cell lines with other aberrations no expression of any of the three miRNAs was noted (FIG. 4). These cell lines were used to quantify the expression of another member of the C19MC cluster, i.e. miR-520c by real-time PCR (qRT-PCR). Akin to the results obtained for the other members of that cluster high expression was noted only in the same four cell lines with 19q13 rearrangements expressing miR-512-5p, miR-517a, and miR-519a (FIG. 5a) whereas a significantly lower expression was seen in the remaining cell lines (p-value=0,001659; for details see Table 3).

TABLE 3

Statistical analysis of the qRT-PCR data.

| 19q translocation | without 19q translocation | microRNA | p-value | d.f. | t |
|---|---|---|---|---|---|
| adenoma | normal thyroid and adenoma | mir371-3p | 0.005355 | 4.48 | 5.0446 |
|  |  | mir372 | 2.232e−06 | 10.996 | 8.9445 |
|  |  | mir373 | 0.006122 | 8.522 | 3.6176 |
|  |  | mir520c | 1.722e−09 | 10.977 | 17.9765 |
| adenoma | adenoma | mir371-3p | 0.004623 | 5.203 | 4.745 |
|  |  | mir372 | 0.0001681 | 7.043 | 7.2279 |
|  |  | mir373 | 0.01428 | 7.9 | 3.128 |
|  |  | mir520c | 4.312e−08 | 7.978 | 19.941 |
| adenoma | normal thyroid | mir371-3p | 0.005471 | 4.159 | 5.2956 |
|  |  | mir372 | 0.008832 | 2.826 | 6.5061 |
|  |  | mir373 | 0.02236 | 4.122 | 3.5632 |
|  |  | mir520c | 0.003133 | 2.573 | 10.9875 |
| adenoma cell line | adenoma cell line | mir371-3p | 0.004041 | 4.446 | 5.4488 |
|  |  | mir372 | 0.1121 | 2.4893 | 2.344 |
|  |  | mir373 | 0.08229 | 2.311 | 2.9573 |
|  |  | mir520c | 0.001659 | 4.029 | 7.4811 |

Statistical analysis (t-test, two-tailed) of the expression of miRNAs from the cluster C19MC and miR-371-3 in tissues or cell lines containing 19q13 rearrangements compared to normal thyroid tissue and/or adenomas without 19q13 rearrangements. The data were obtained using statistical software R (www.r-project.org). (d.f.=degrees of freedom, t=Student's tvalue).

Most likely, the exceptionally low expression of all examined members of the C19MC cluster in cell line S121 may result from a deletion of that part of the breakpoint region resulting from the chromosomal translocation. To see if comparable results can be obtained for primary tumors as well 70 thyroid nodules were characterized by interphase fluorescence in situ hybridization (1-FISH) on cytologic samples obtained prior to cell culturing. The results were usually supplemented by conventional cytogenetics. FISH screening of the nodules detected five tumors with clonal rearrangements of chromosomal band 19q13 (FIG. 5). It could be shown that all thyroid adenomas with 19q13 rearrangements express significantly higher levels (p-value ≤0,003133) of miR-520 than samples without 19q13 rearrangements (adenomas and surrounding thyroid tissue; for details see Table 3) (FIG. 5b).

Example 3

Adenomas with 19q13 Aberrations Express Significantly Higher Levels of Members of the miR-371-3 Cluster than Those without that Translocation To see if the 19q13 rearrangements also activate the expression of the miR-371-3 cluster the expression of three members of this cluster was quantified in the same samples used before. All tumors with 19q13 rearrangements were shown to express significantly higher levels of miR-371-3p, miR-372, and miR-373 than three samples of surrounding histologically normal thyroid tissue (p-value ≤0,02236;) and the five cytogenetically normal adenomas (p-value ≤0,01428;) (FIG. 5c). Then the expression of miR-371-3p, miR-372, and miR-373 was quantified in the cell lines where comparable results were obtained (FIG. 5d). Interestingly, cell line S121 with absent or very low expression of the C19MC cluster members showed a high expression of the miR-371-3 cluster thus further strengthening the idea that in this cell line part of the C19MC cluster is deleted.

Example 4

Translocation of Proximal Part of Pumillo Homolog 1 (PUM1) Gene Activates C19MC and miR-371-3 Cluster In order to further understand the mechanisms involved in the activation of the miRNA clusters one cell line of the 19q13 group has been investigated in more detail. This cell line shows a rearrangement of chromosomal band 19q13.4 resulting from an apparently balanced translocation t(1;19) (1p35.2;q13.4) (FIG. 6). By appropriate BAC (bacterial artificial chromosome) probes the breakpoint on chromosome 1 was narrowed down to a region within pumilio homolog 1 (PUM1) (FIG. 7 online). PUM1 encodes a RNA-binding protein and shows a widespread expression in adult tissues. It has 22 exons and spans about 150 kb on chromosomal band 1p35.2 (Spassov and Jurecic, Gene 299 (2002), 195-204; Szabo et al., Genome Biol. 5 (2004), R59). By the translocation the proximal part of PUM1 becomes juxtaposed to the miRNA clusters (FIG. 6). Therefore 3'RACE-PCR was used to detect possible fusion transcripts between the proximal part of PUM1 and sequences from chromosome 19. First, it was possible to detect a fusion transcript consisting of exon 1-10 of PUM1 followed by an ectopic sequence of the chromosome 19 breakpoint region (submitted to GenBank GQ334687). From the existence of this transcript it was concluded that the chromosomal break in this cell line is located within intron 10 of PUM1. Accordingly, RT-PCR experiments were performed using a sequence within exon 10 as the forward primer (Primer: Ex9_Up (Exon 10 of PUM1) CAA-CAGACCACCCCACAGGCTCAG and Primer after C19MC: 500-Cluster_PolyA_I CAACCGTTGGGGATTA-CAAAATAGA (SEQ ID NOs: 138 and 139)) by which it was possible to detect part of one fusion transcript with a border clearly extending the distal border of C19MC (gene bank accession no. GQ334688; FIG. 6). From these results it seems reasonable to assume that in the cell line S40.2 both clusters become part of large Pol-II transcript driven by the PUM1 promoter. Activation by an ectopic Pol-II promoter may generally be the mechanism by which the translocations activate both miRNA clusters and fits with the apparent "natural" generation of the miRNAs of the C19MC cluster from a large Pol-II driven transcript as with the results of a recent study (Bortolin-Cavaille et al., J. Nucleic Acids Res. 37, (2009) 3464-73).

Example 5

Tumors Involving Chromosomal Translocation Associated with the Activation of miR Clusters From the histologic analyses performed herein no evidence for invasiveness of the corresponding tumors has been found that by definition would lead to the diagnosis of a follicular carcinoma. Also, no other differences compared to adenomas without the 19q-rearrangement became apparent. Balanced translocations involving 19q13.4 have also been described in mesenchymal hamartoma of the liver (MHL), a rare benign tumor-like lesion of childhood (Speleman et al., Cancer Genet. Cytogenet. 40 (1989), 29-32) and more generally, breaks of chromosomal band 19q13 have been reported in a variety of human neoplasms (e.g. small cell lung carcinoma or colon carcinoma). Furthermore, according to the Cancer-Chromosomes/Mitelman database (NCBI) chromosomal band 19q13 belongs to the areas most frequently targeted by chromosomal aberrations at all in the genome. Thus, it remains to be determined whether or not some of these do also target either of the two or both miRNA clusters investigated herein. However, there is ample evidence that within the thyroid epithelium the clonal re-expression of two important "embryonic" miRNA clusters with thousands of potential targets is causally linked to the development of a large subgroup of thyroid adenomas. Effects of individual of these miRNAs with single targets have been associated with human tumors but mechanistically the effects observed are more likely to result from global changes of gene expression than from the de-regulation of single targets of the corresponding miRNAs.

Hence, the experiments performed in a accordance with the present invention make miRs of the C19MC and miR-371-3 cluster most likely target genes of a highly frequent chromosomal rearrangement in epithelial tumors. Furthermore, this is the first evidence correlating a common chromosomal rearrangement with the activation of a miRNA gene or a miRNA cluster, respectively. Accordingly, it is prudent to expect miRs, in particular those belonging to a miR cluster located in proximity to a breakpoint region to represent a valuable diagnostic and therapeutic tool in the treatment of tumors involving such chromosomal rearrangements.

Example 6

Expression of the Two Stem Cell microRNA Gene Clusters C19MC and miR-371-3 in Tumors and Different Tumor Cell Lines, Respectively Total RNA was isolated from cell lines and tumor tissue using QIAGEN miRNEasy Mini Kit (QIAGEN, Hilden, Germany) according to the manufacturer's instructions.

miRNA (miR-371-3p, miR-372, miR-373, miR-520c and miR-103)-specific cDNA were generated from 200 ng of total RNA using the TaqMan microRNA RT Kit and the gene-specific RT primers from the TaqMan microRNA Assays (Applied Biosystems, Foster City, Calif., USA) according to the manufacturer's instructions. miR-103 served as endogenous control for relative quantification. The reactions were incubated in a thermal cycler for 30 min at 16° C., 30 min at 42° C., 5 min at 85° C. and then stored at 4° C. All reverse transcriptions included no-template controls and minus RT controls (-RT).

Real-time PCR was performed using an Applied Biosystems 7300 Fast Real Time PCR system with miRNA specific probes and TaqMan Universal PCR Master Mix (Applied Biosystems, Foster City, Calif., USA). The reactions were incubated in 96-well plates at 95° C. for 10 min followed by 40 cycles of 15 s at 95° C. and one min at 60° C. All reactions were run in triplicate.

Relative quantification (RQ) was calculated using Applied Biosystems SDS software based on the $RQ=2^{-\Delta\Delta Ct}$ method. Ct values were normalized to the internal control miR-103.

Relative expression of miRNAs of both clusters was determined by qRT-PCR in two thyroid adenoma tissues (one without 19q13.4 rearrangement (S925) and one with 19q13.4 rearrangement (S958)), one cell line derived from thyroid adenoma with 19q13.4 rearrangement (S40.2) as well as ten different tumor derived cell lines (all without 19q13.4 rearrangements).

Results

The results are indicated in FIGS. 8 to 11.

Both samples with 19q13.4 rearrangement (the thyroid adenoma tissue S958 and the thyroid adenoma derived cell line S40.2) showed high expression levels of all measured miRNAs of both clusters. The expression levels of these miRNAs were also slightly increased in the cervical cancer cell line MRIH-215.

Example 7

Expression of the Two Stem Cell microRNA Gene Clusters C19MC and miR-371-3 in Cells Cultures from Placenta Cells Obtained by Chorionic Villi Sampling Total RNA was isolated from cultured chorionic villi cells using QIAGEN miRNEasy Mini Kit (QIAGEN, Hilden, Germany) according to the manufacturer's instructions.

miRNA (miR-371-3p, miR-372, miR-373, miR-520c and miR-103)-specific cDNA were generated from 200 ng of total RNA using the TaqMan microRNA RT Kit and the gene-specific RT primers from the TaqMan microRNA Assays (Applied Biosystems, Foster City, Calif., USA) according to the manufacturer's instructions. miR-103 served as endogenous control for relative quantification. The reactions were incubated in a thermal cycler for 30 min at 16° C., 30 min at 42° C., 5 min at 85° C. and then stored at 4° C. All reverse transcriptions included no-template controls and minus RT controls (-RT).

Real-time PCR was performed using an Applied Biosystems 7300 Fast Real Time PCR system with miRNA specific probes and TaqMan Universal PCR Master Mix (Applied Biosystems, Foster City, Calif., USA). The reactions were incubated in 96-well plates at 95° C. for 10 min followed by 40 cycles of 15 s at 95° C. and one min at 60° C. All reactions were run in triplicate. Relative quantification (RQ) was calculated using Applied Biosystems SDS software based on the $RQ=2^{-\Delta\Delta Ct}$ method. Ct values were normalized to the internal control miR-103.

Relative expression of miRNAs of both clusters was determined by qRT-PCR in two thyroid adenoma tissues (one without 19q13.4 rearrangement (S925) and one with 19q13.4 rearrangement (S958)), one cell line derived from thyroid adenoma with 19q13.4 rearrangement (S40.2) as well as eight different cultured chorionic villi (first and/or second passage).

Results

The results are depicted in FIGS. 12 to 15.

Both samples with 19q13.4 rearrangement (the thyroid adenoma tissue 5958 and the thyroid adenoma derived cell line S40.2) showed high expression levels of all measured miRNAs of both clusters.

High expression levels of the miRNAs of the cluster miR-371-3 were also detected in all chorionic villi samples except for Fi 92. Interestingly, cytogenetic analysis of this sample revealed an 45,X0 karyotype (Turner syndrome).

Expression of miR-520c-3p of the cluster C19MC was high in all chorionic villi samples except for Fi 156 and Fi 160 (both first and second passage) which only showed a slightly increased expression level.

The features of the present invention disclosed in the specification, the claims, the sequence listing and/or the drawings may both separately and in any combination thereof be material for realizing the invention in various forms thereof.

The invention claimed is:

1. A method of diagnosing whether a subject has, or is at risk for developing a tumor or neoplasia of the thyroid gland with a chromosomal rearrangement on chromosomal band 19q13, the method comprising measuring the level of at least one microRNA (miR) in a test sample from the subject, wherein the presence or increased level of the miR in the test sample, relative to the level of a corresponding miR in a control sample, is indicative of the subject either having, or being at risk for developing said tumor or neoplasia of the thyroid gland, wherein said at least one miR is part of the C19MC cluster or the miR-373-3 cluster.

2. The method of claim 1, wherein the chromosomal rearrangement is a translocation.

3. The method of claim 1, wherein said measuring the level of at least one miR comprises measuring the level of at least one miR of the C19MC cluster and at least one miR of the miR-371-3 cluster.

4. The method of claim 1, wherein the at least one miR comprises one or more of hsa-mir-371; hsa-miR-37-3p; hsa-miR-371-5p; hsa-miR-372; hsa-miR-373; hsa-miR-373*; hsa-mir-512-1; hsa-miR-512-5p; hsa-miR-512-3p; hsa-mir-512-2; hsa-miR-512-5p; hsa-miR-512-3p; hsa-mir-515-1; hsa-miR-515-5p; hsa-miR-515-3p; hsa-mir-515-2; hsa-miR-515-5p; hsa-miR-515-3p; hsa-mir-516a-1; hsa-miR-516a-5p; hsa-miR-516a-3p; hsa-mir-516a-2; hsa-miR-516a-5p; hsa-miR-516a-3p; hsa-mir-516b-1; hsa-miR-516b; hsa-miR-516b*; hsa-mir-518b; hsa-miR-517a; hsa-miR-517*; hsa-miR-517b; hsa-miR-517*; hsa-mir-517c; hsa-miR-517*; hsa-mir-518a-1; hsa-miR-518a-5p; hsa-miR-518a-3p; hsa-mir-518a-2; hsa-miR-518a-5p; hsa-miR-518a-3p; hsa-miR-518b; hsa-miR-518c; hsa-miR-518c*; hsa-mir-518d; hsa-miR-518d-5p; hsa-miR-518d-3p; hsa-miR-518e; hsa-miR-518e*; hsa-mir-518f; hsa-miR-518f*; hsa-mir-519a-1; hsa-miR-519a; hsa-miR-519a*; hsa-mir-519a-2; hsa-mir-519b; hsa-miR-519b-5p; hsa-miR-519b-3p; hsa-miR-519c; hsa-miR-519c-5p; hsa-miR-519c-3p; hsa-miR-519d; hsa-mir-519e; hsa-miR-519e; hsa-miR-519e*; hsa-mir-520a; hsa-miR-520a-5p; hsa-miR-520a-3p; hsa-miR-520b; hsa-mir-520c; hsa-miR-520c-5p; hsa-miR-520c-3p; hsa-mir-520d; hsa-miR-520d-5p; hsa-miR-520d-3p; hsa-miR-520e; hsa-miR-520f; hsa-miR-520g; hsa-miR-520h; hsa-mir-521-1; hsa-mir-521-2; hsa-miR-521; hsa-mir-522; hsa-miR-522*; hsa-mir-523; hsa-miR-523*; hsa-mir-524; hsa-miR-524-5p; hsa-miR-524-3p; hsa-mir-525; hsa-miR-525-5p; hsa-miR-525-3p; hsa-mir-526a-1; hsa-miR-526a; hsa-miR-526a-2; hsa-miR-526b; hsa-miR-526b*; and hsa-miR-527.

5. The method of claim 1, wherein the tumor is a thyroid adenoma.

6. The method of claim 1, wherein the tumor is associated with one or more prognostic markers in a subject.

7. The method of claim 6, wherein the tumor is thyroid adenoma and the prognostic marker is trisomy 7.

8. The method of claim 1, wherein the subject is a human.

9. The method of claim 1, wherein said at least one miR comprises at least one of miR-512-5p, miR-517a, miR-519a, miR-520c, miR-371-3p, miR-372 and/or miR-373.

10. The method of claim 1, wherein said at least one miR comprises miR-371-3p.

11. The method of claim 1, wherein said at least one miR comprises miR-3712-5p.

12. The method of claim 1, wherein said at least one miR comprises miR-517a.

13. The method of claim 1, wherein said at least one miR comprises miR-519a.

14. The method of claim 1, wherein said at least one miR comprises miR-520c.

15. The method of claim 1, wherein said at least one miR comprises miR-373.

* * * * *

SEQUENCE LISTING

<160> NUMBER OF SEQ ID NOS: 162

<210> SEQ ID NO 1
<211> LENGTH: 67
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 1
guggcacuca aacugugggg gcacuuucug cucucuggug aaagugccgc caucuuuga      60 guguuac                                                               67

<210> SEQ ID NO 2
<211> LENGTH: 23
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 2
aagugccgcc aucuuugag ugu                                              23

<210> SEQ ID NO 3
<211> LENGTH: 20
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 3
acucaaacug uggggggcacu                                                20

<210> SEQ ID NO 4
<211> LENGTH: 67
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 4
gugggccuca aauguggagc acuauucuga uguccaagug gaaagugcug cgacauuga      60 gcgucac                                                               67

<210> SEQ ID NO 5
<211> LENGTH: 23
<212> TYPE: RNA
<213> ORGANISM: Homo sapiens
<220> FEATURE:
<221> NAME/KEY: misc_feature
<223> OTHER INFORMATION: miRNA
<220> FEATURE:

```
<221> NAME/KEY: misc_feature
<223> OTHER INFORMATION: mature

<400> SEQUENCE: 5
aaagugcugc gacauuugag cgu                                              23

<210> SEQ ID NO 6
<211> LENGTH: 69
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 6
gggauacuca aaauggggc gcuuccuuu uugucuguac ugggaagugc uucgauuuug         60
gggguguccc                                                             69

<210> SEQ ID NO 7
<211> LENGTH: 23
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 7
gaagugcuuc gauuuugggg ugu                                              23

<210> SEQ ID NO 8
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 8
acucaaaaug ggggcgcuuu cc                                               22

<210> SEQ ID NO 9
<211> LENGTH: 84
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 9
ucucagucug uggcacucag ccuugagggc acuuucuggu gccagaauga aagugcuguc       60
auagcugagg uccaaugacu gagg                                             84

<210> SEQ ID NO 10
<211> LENGTH: 23
<212> TYPE: RNA
```

```
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 10
cacucagccu ugagggcacu uuc                                             23

<210> SEQ ID NO 11
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 11
aagugcuguc auagcugagg uc                                              22

<210> SEQ ID NO 12
<211> LENGTH: 98
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 12
gguacuucuc agucugugge acucagccuu gagggcacuu ucuggugcca gaaugaaagu     60
gcugucauag cugaggucca augacugagg cgagcacc                             98

<210> SEQ ID NO 13
<211> LENGTH: 23
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 13
cacucagccu ugagggcacu uuc                                             23

<210> SEQ ID NO 14
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 14
aagugcuguc auagcugagg uc                                              22
```

```
<210> SEQ ID NO 15
<211> LENGTH: 83
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 15
ucucaugcag ucauucucca aaagaaagca cuuucuguug ucgaaagca gagugccuuc    60 uuuuggagcg uuacuguuug aga                                          83

<210> SEQ ID NO 16
<211> LENGTH: 24
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 16
uucuccaaaa gaaagcacuu ucug                                         24

<210> SEQ ID NO 17
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 17
gagugccuuc uuuuggagcg uu                                           22

<210> SEQ ID NO 18
<211> LENGTH: 83
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 18
ucucaugcag ucauucucca aaagaaagca cuuucuguug ucgaaagca gagugccuuc    60 uuuuggagcg uuacuguuug aga                                          83

<210> SEQ ID NO 19
<211> LENGTH: 24
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature
```

```
<400> SEQUENCE: 19
uucuccaaaa gaaagcacuu ucug                                              24

<210> SEQ ID NO 20
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 20
gagugccuuc uuuuggagcg uu                                                22

<210> SEQ ID NO 21
<211> LENGTH: 90
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 21
ucucaggcug ugaccuucuc gaggaaagaa gcacuuucug uugucugaaa gaaaagaaag       60
ugcuuccuuu cagagdgguua cgguuugaga                                       90

<210> SEQ ID NO 22
<211> LENGTH: 23
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 22
uucucgagga aagaagcacu uuc                                               23

<210> SEQ ID NO 23
<211> LENGTH: 18
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 23
ugcuuccuuu cagagggu                                                     18

<210> SEQ ID NO 24
<211> LENGTH: 90
<212> TYPE: RNA
<213> ORGANISM: Homo sapiens
<220> FEATURE:
<221> NAME/KEY: misc_feature
<223> OTHER INFORMATION: miRNA
<220> FEATURE:
```

-continued

```
<221> NAME/KEY: misc_feature
<223> OTHER INFORMATION: Stem-loop

<400> SEQUENCE: 24
ucucagguug ugaccuucuc gaggaaagaa gcacuuucug uugcugaaa gaaaagaaag    60 ugcuuccuuu cagagdguua cgguuugaga                                   90

<210> SEQ ID NO 25
<211> LENGTH: 23
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 25
uucucgagga aagaagcacu uuc                                          23

<210> SEQ ID NO 26
<211> LENGTH: 18
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 26
ugcuuccuuu cagagggu                                                18

<210> SEQ ID NO 27
<211> LENGTH: 90
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 27
ucucaggcug ugaccaucug gagguaagaa gcacuuucug uuuugugaaa gaaaagaaag   60
ugcuuccuuu cagagdguua cucuuugaga                                   90

<210> SEQ ID NO 28
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 28
aucuggaggu aagaagcacu uu                                           22

<210> SEQ ID NO 29
<211> LENGTH: 18
<212> TYPE: RNA
```

```
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 29
ugcuuccuuu cagagggu                                                   18

<210> SEQ ID NO 30
<211> LENGTH: 85
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 30
ucucaugaug ugaccaucug gagguaagaa gcacuuugug uuuugugaaa gaaagugcuu     60
ccuuucagag gguuacucuu ugaga                                           85

<210> SEQ ID NO 31
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 31
aucuggaggu aagaagcacu uu                                              22

<210> SEQ ID NO 32
<211> LENGTH: 18
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 32
ugcuuccuuu cagagggu                                                   18

<210> SEQ ID NO 33
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 33
ucucaggcag ugacccucua gauggaagca cugucuguug uauaaaagaa aagaucgugc     60 auccuuuag aguguuacug uuugaga                                          87
```

```
<210> SEQ ID NO 34
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 34
aucgugcauc ccuuuagagu gu                                              22

<210> SEQ ID NO 35
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 35
ccucuagaug gaagcacugu cu                                              22

<210> SEQ ID NO 36
<211> LENGTH: 67
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 36
gugacccucu agauggaagc acugucuguu gucuaagaaa agaucgugca ucccuuuaga     60
guguuac                                                              67

<210> SEQ ID NO 37
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 37
ucgugcaucc cuuuagagug uu                                              22

<210> SEQ ID NO 38
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor
```

```
<400> SEQUENCE: 38
ccucuagaug gaagcacugu cu                                              22

<210> SEQ ID NO 39
<211> LENGTH: 95
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 39
gaagaucuca ggcagugacc cucuagaugg aagcacuguc uguugcuaa gaaaagaucg      60 ugcauccuuu uagaguguua cuguuugaga aaauc                                95

<210> SEQ ID NO 40
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 40
aucgugcauc cuuuuagagu gu                                              22

<210> SEQ ID NO 41
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 41
ccucuagaug gaagcacugu cu                                              22

<210> SEQ ID NO 42
<211> LENGTH: 85
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 42
ucucaagcug ugacugcaaa gggaagcccu uucuguuguc ugaaagaaga gaaagcgcuu     60
cccuuugcug gauuacgguu ugaga                                           85

<210> SEQ ID NO 43
<211> LENGTH: 20
<212> TYPE: RNA
<213> ORGANISM: Homo sapiens
<220> FEATURE:
<221> NAME/KEY: misc_feature
```

```
<223> OTHER INFORMATION: miRNA
<220> FEATURE:
<221> NAME/KEY: misc_feature
<223> OTHER INFORMATION: mature

<400> SEQUENCE: 43
cugcaaaggg aagcccuuuc                                              20

<210> SEQ ID NO 44
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 44
gaaagcgcuu cccuuugcug ga                                           22

<210> SEQ ID NO 45
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 45
ucucaagcug ugggucugca aagggaagcc cuuucuguug ucuaaaagaa gagaaagcgc   60
uucccuuugc uggauuacgg uuugaga                                      87

<210> SEQ ID NO 46
<211> LENGTH: 20
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 46
cugcaaaggg aagcccuuuc                                              20

<210> SEQ ID NO 47
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 47
gaaagcgcuu cccuuugcug ga                                           22

<210> SEQ ID NO 48
<211> LENGTH: 83
<212> TYPE: RNA
```

```
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 48
ucaugcugug gcccuccaga gggaagcgcu uucuguuguc ugaaagaaaa caaagcgcuc    60
cccuuuagag guuuacgguu uga                                           83

<210> SEQ ID NO 49
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 49
caaagcgcuc cccuuuagag gu                                            22

<210> SEQ ID NO 50
<211> LENGTH: 101
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 50
gcgagaagau cucaugcugu gacucucugg agggaagcac uuucuguugu cugaaagaaa    60
acaaagcgcu ucucuuuaga guguuacggu uugagaaaag c                      101

<210> SEQ ID NO 51
<211> LENGTH: 23
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 51
caaagcgcuu cucuuuagag ugu                                           23

<210> SEQ ID NO 52
<211> LENGTH: 23
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 52
ucucuggagg gaagcacuuu cug                                           23
```

<210> SEQ ID NO 53
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 53
ucccaugcug ugacccucua gagggaagca cuuucuguug ucugaaagaa accaaagcgc    60
uucccuuugg agcguuacgg uuugaga                                       87

<210> SEQ ID NO 54
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 54
cucuagaggg aagcacuuuc ug                                            22

<210> SEQ ID NO 55
<211> LENGTH: 21
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 55
caaagcgcuu cccuuuggag c                                             21

<210> SEQ ID NO 56
<211> LENGTH: 88
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 56
ucucaggcug ugacccucua gagggaagcg cuuucuguug gcuaaaagaa aagaaagcgc    60
uucccuucag aguguuaacg cuuugaga                                      88

<210> SEQ ID NO 57
<211> LENGTH: 21
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature

```
<223> OTHER INFORMATION: mature

<400> SEQUENCE: 57
aaagcgcuuc ccuucagagu g                                              21

<210> SEQ ID NO 58
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 58
cucuagaggg aagcgcuuuc ug                                             22

<210> SEQ ID NO 59
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 59
ucucaugcug ugacccucua gagggaagca cuuucucuug ucuaaaagaa aagaaagcgc     60
uucucuuuag aggauuacuc uuugaga                                        87

<210> SEQ ID NO 60
<211> LENGTH: 21
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 60
gaaagcgcuu cucuuuagag g                                              21

<210> SEQ ID NO 61
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 61
cucuagaggg aagcacuuuc uc                                             22

<210> SEQ ID NO 62
<211> LENGTH: 85
<212> TYPE: RNA
<213> ORGANISM: Homo sapiens
<220> FEATURE:
<221> NAME/KEY: misc_feature
```

```
<223> OTHER INFORMATION: miRNA
<220> FEATURE:
<221> NAME/KEY: misc_feature
<223> OTHER INFORMATION: Stem-loop

<400> SEQUENCE: 62
cucaggcugu gacacucuag agggaagcgc uuucuguugu cugaaagaaa ggaaagugca    60
uccuuuuaga guguuacugu uugag                                         85

<210> SEQ ID NO 63
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 63
aaagugcauc cuuuuagagu gu                                            22

<210> SEQ ID NO 64
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 64
cucuagaggg aagcgcuuuc ug                                            22

<210> SEQ ID NO 65
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 65
ucucaggcug ugucccucua cagggaagcg cuuucuguug ucugaaagaa aggaaagugc    60
auccuuuuag aguguuacug uuugaga                                       87

<210> SEQ ID NO 66
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 66
aaagugcauc cuuuuagagu gu                                            22

<210> SEQ ID NO 67
```

```
<211> LENGTH: 81
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 67
caugcuguga cccucuagag ggaagcgcuu ucuguugucu gaaagaaaag aaagugcauc      60
cuuuuagagg uuuacuguuu g                                               81

<210> SEQ ID NO 68
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 68
cucuagaggg aagcgcuuuc ug                                              22

<210> SEQ ID NO 69
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 69
aaagugcauc cuuuuagagg uu                                              22

<210> SEQ ID NO 70
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 70
ucucagccug ugacccucua gagggaagcg cuuucuguug ucugaaagaa aagaaagugc      60
aucuuuuuag aggauuacag uuugaga                                         87

<210> SEQ ID NO 71
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 71
```

```
cucuagaggg aagcgcuuuc ug                                                22
```

<210> SEQ ID NO 72
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 72

```
aaagugcauc uuuuuagagg au                                                22
```

<210> SEQ ID NO 73
<211> LENGTH: 88
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 73

```
ucccaugcug ugacccucca aagggaagcg cuuucuguuu guuucucuu aaacaaagug        60 ccucccuuua gaguguuacc guuuggga                                          88
```

<210> SEQ ID NO 74
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 74

```
caaagugccu cccuuuagag ug                                                22
```

<210> SEQ ID NO 75
<211> LENGTH: 84
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 75

```
ucucaugcag ucauucucca aagggagca cuuucuguuu gaaagaaaac aaagugccuc        60
cuuuuagagu guuacuguuu gaga                                              84
```

<210> SEQ ID NO 76
<211> LENGTH: 22
<212> TYPE: RNA
<213> ORGANISM: Homo sapiens
<220> FEATURE:
<221> NAME/KEY: misc_feature
<223> OTHER INFORMATION: miRNA -continued

```
<220> FEATURE:
<221> NAME/KEY: misc_feature
<223> OTHER INFORMATION: mature

<400> SEQUENCE: 76
aagugccucc uuuuagagug uu                                               22

<210> SEQ ID NO 77
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 77
uucuccaaaa gggagcacuu uc                                               22

<210> SEQ ID NO 78
<211> LENGTH: 85
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 78
cucaggcugu gacccuccag agggaaguac uuucuguugu cugagagaaa agaaagugcu     60
ucccuuugga cuguuucggu uugag                                           85

<210> SEQ ID NO 79
<211> LENGTH: 21
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 79
cuccagaggg aaguacuuuc u                                                21

<210> SEQ ID NO 80
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 80
aaagugcuuc ccuuuggacu gu                                               22

<210> SEQ ID NO 81
<211> LENGTH: 61
<212> TYPE: RNA
<213> ORGANISM: Homo sapiens
```

```
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 81
cccucuacag ggaagcgcuu ucuguugucu gaaagaaaag aaagugcuuc cuuuuagagg      60
g                                                                     61

<210> SEQ ID NO 82
<211> LENGTH: 21
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 82
aaagugcuuc cuuuuagagg g                                               21

<210> SEQ ID NO 83
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 83
ucucaggcug ucguccucua gagggaagca cuuucuguug ucugaaagaa aagaaagugc      60
uuccuuuuag aggguuaccg uuugaga                                         87

<210> SEQ ID NO 84
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 84
cucuagaggg aagcacuuuc ug                                              22

<210> SEQ ID NO 85
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 85
aaagugcuuc cuuuuagagg gu                                              22
```

```
<210> SEQ ID NO 86
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 86
ucucaagcug ugagucuaca aagggaagcc cuuucuguug ucuaaaagaa aagaaagugc    60
uucucuuugg uggguuacgg uuugaga                                       87

<210> SEQ ID NO 87
<211> LENGTH: 20
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 87
cuacaaaggg aagcccuuuc                                               20

<210> SEQ ID NO 88
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 88
aaagugcuuc ucuuuggugg gu                                            22

<210> SEQ ID NO 89
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 89
ucuccugcug ugaccccucaa gauggaagca guuucuguug ucugaaagga aagaaagugc    60
uuccuuuuug aggguuacug uuugaga                                       87

<210> SEQ ID NO 90
<211> LENGTH: 21
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature
```

```
<400> SEQUENCE: 90
aaagugcuuc cuuuuugagg g                                              21

<210> SEQ ID NO 91
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 91
ucucaggcug ugacccucua aagggaagcg cuuucugugg ucagaaagaa aagcaagugc     60
uuccuuuuag aggguuaccg uuuggga                                        87

<210> SEQ ID NO 92
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 92
aagugcuucc uuuuagaggg uu                                             22

<210> SEQ ID NO 93
<211> LENGTH: 90
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 93
ucccaugcug ugacccucua gaggaagcac uuucuguuug uugucugaga aaaacaaag     60 ugcuucccuu uagaguguua ccguuuggga                                     90

<210> SEQ ID NO 94
<211> LENGTH: 24
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 94
acaaagugcu ucccuuuaga gugu                                           24

<210> SEQ ID NO 95
<211> LENGTH: 88
<212> TYPE: RNA
<213> ORGANISM: Homo sapiens
<220> FEATURE:
```

```
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 95
ucccaugcug ugacccucua gaggaagcac uuucuguuug uugucugaga aaaaacaaag    60
ugcuucccuu uagaguuacu guuuggga                                      88

<210> SEQ ID NO 96
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 96
acaaagugcu ucccuuuaga gu                                            22

<210> SEQ ID NO 97
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 97
ucucaggcug ugacccucca aagggaagaa cuuucguuug ucuaaaagaa aagaacgcac    60
uucccuuuag aguguuaccg ugugaga                                       87

<210> SEQ ID NO 98
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 98
aacgcacuuc ccuuuagagu gu                                            22

<210> SEQ ID NO 99
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 99
ucucgggcug ugacucucca aagggaagaa uuucucuuug ucuaaaagaa aagaacgcac    60
uucccuuuag aguguuaccg ugugaga                                       87
```

```
<210> SEQ ID NO 100
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 100
aacgcacuuc ccuuuagagu gu                                              22

<210> SEQ ID NO 101
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 101
ucucaggcug uguccucucua gagggaagcg cuuucuguug ucugaaagaa aagaaaaugg    60
uucccuuuag aguguuacgc uuugaga                                         87

<210> SEQ ID NO 102
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 102 aaaauggouuc ccuuuagagu gu                                             22

<210> SEQ ID NO 103
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 103
cucuagaggg aagcgcuuuc ug                                              22

<210> SEQ ID NO 104
<211> LENGTH: 87
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop
```

-continued

```
<400> SEQUENCE: 104
ucucaugcug ugacccucua gagggaagcg cuuucuguug ucugaaagaa aagaacgcgc    60
uucccuauag aggguuaccc uuugaga                                       87

<210> SEQ ID NO 105
<211> LENGTH: 23
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 105
gaacgcgcuu cccuauagag ggu                                           23

<210> SEQ ID NO 106
<211> LENGTH: 22
<212> TYPE: RNA
<213> ORGANISM: Homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 106
cucuagaggg aagcgcuuuc ug                                            22

<210> SEQ ID NO 107
<211> LENGTH: 87
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 107
ucucaugcug ugacccuaca aagggaagca cuuucucuug uccaaaggaa aagaaggcgc    60
uucccuuugg aguguuacgg uuugaga                                       87

<210> SEQ ID NO 108
<211> LENGTH: 22
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 108
cuacaaaggg aagcacuuuc uc                                            22

<210> SEQ ID NO 109
<211> LENGTH: 21
<212> TYPE: RNA
<213> ORGANISM: homo sapiens
<220> FEATURE:
<221> NAME/KEY: misc_feature
```

<223> OTHER INFORMATION: miRNA
<220> FEATURE:
<221> NAME/KEY: misc_feature
<223> OTHER INFORMATION: mature

<400> SEQUENCE: 109
gaaggcgcuu cccuuuggag u                                              21

<210> SEQ ID NO 110
<211> LENGTH: 85
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 110
cucaagcugu gacucuccag agggaugcac uuucucuuau gugaaaaaaa agaaggcgcu    60
ucccuuuaga gcguuacggu uuggg                                          85

<210> SEQ ID NO 111
<211> LENGTH: 21
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 111
cuccagaggg augcacuuuc u                                              21

<210> SEQ ID NO 112
<211> LENGTH: 22
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 112
gaaggcgcuu cccuuuagag cg                                             22

<210> SEQ ID NO 113
<211> LENGTH: 85
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 113
cucaggcugu gacccucuag agggaagcac uuucuguugc uugaagaag agaaagcgcu     60 uccuuuuaga ggauuacucu uugag                                          85

<210> SEQ ID NO 114

```
<211> LENGTH: 22
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 114
cucuagaggg aagcacuuuc ug                                              22

<210> SEQ ID NO 115
<211> LENGTH: 65
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 115
gugacccucu agagggaagc acuuucuguu gaaagaaaag aacaugcauc cuuucagagg      60
guuac                                                                 65

<210> SEQ ID NO 116
<211> LENGTH: 22
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 116
cucuagaggg aagcacuuuc ug                                              22

<210> SEQ ID NO 117
<211> LENGTH: 83
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 117
ucaggcugug acccucuuga gggaagcacu uucuguuguc ugaaagaaga gaaagugcuu      60
ccuuuuagag gcuuacuguc uga                                             83

<210> SEQ ID NO 118
<211> LENGTH: 23
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 118
```

-continued cucuugaggg aagcacuuuc ugu    23

<210> SEQ ID NO 119
<211> LENGTH: 22
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: minor

<400> SEQUENCE: 119
gaaagugcuu ccuuuuagag gc    22

<210> SEQ ID NO 120
<211> LENGTH: 85
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: Stem-loop

<400> SEQUENCE: 120
ucucaagcug ugacugcaaa gggaagcccu uucuguuguc uaaaagaaaa gaaagugcuu    60
cccuuuggug aauuacgguu ugaga    85

<210> SEQ ID NO 121
<211> LENGTH: 20
<212> TYPE: RNA
<213> ORGANISM: homo sapiens
<220> FEATURE:
<221> NAME/KEY: misc_feature
<223> OTHER INFORMATION: miRNA
<220> FEATURE:
<221> NAME/KEY: misc_feature
<223> OTHER INFORMATION: mature

<400> SEQUENCE: 121
cugcaaaggg aagcccuuuc    20

<210> SEQ ID NO 122
<211> LENGTH: 26
<212> TYPE: DNA
<213> ORGANISM: Artificial
<220> FEATURE:
<223> OTHER INFORMATION: synthetic

<400> SEQUENCE: 122
ccctcaagaa ccagctaatc ccaaca    26

<210> SEQ ID NO 123
<211> LENGTH: 23
<212> TYPE: DNA
<213> ORGANISM: Artificial
<220> FEATURE:
<223> OTHER INFORMATION: synthetic

<400> SEQUENCE: 123
ttcctgggtg atcaatggcg aga    23

<210> SEQ ID NO 124

```
<211> LENGTH: 20
<212> TYPE: DNA
<213> ORGANISM: Artificial
<220> FEATURE:
<223> OTHER INFORMATION: synthetic

<400> SEQUENCE: 124
tccccgggcg attcctgtct                                              20

<210> SEQ ID NO 125
<211> LENGTH: 26
<212> TYPE: DNA
<213> ORGANISM: Artificial
<220> FEATURE:
<223> OTHER INFORMATION: synthetic

<400> SEQUENCE: 125
tccatcacat caccctcctc cttcaa                                       26

<210> SEQ ID NO 126
<211> LENGTH: 21
<212> TYPE: DNA
<213> ORGANISM: Artificial
<220> FEATURE:
<223> OTHER INFORMATION: synthetic

<400> SEQUENCE: 126
acctaatgcg cttgctgtcc a                                            21

<210> SEQ ID NO 127
<211> LENGTH: 19
<212> TYPE: DNA
<213> ORGANISM: Artificial
<220> FEATURE:
<223> OTHER INFORMATION: synthetic

<400> SEQUENCE: 127
gctcccgctg cgtttgtcc                                               19

<210> SEQ ID NO 128
<211> LENGTH: 24
<212> TYPE: DNA
<213> ORGANISM: Artificial
<220> FEATURE:
<223> OTHER INFORMATION: synthetic

<400> SEQUENCE: 128
caacagacca ccccacaggc tcag                                         24

<210> SEQ ID NO 129
<211> LENGTH: 34
<212> TYPE: DNA
<213> ORGANISM: Artificial
<220> FEATURE:
<223> OTHER INFORMATION: synthetic

<400> SEQUENCE: 129
aaggatccgt cgacatcttt tttttttttt tttt                              34

<210> SEQ ID NO 130
<211> LENGTH: 60
<212> TYPE: DNA
<213> ORGANISM: Artificial
<220> FEATURE:
<223> OTHER INFORMATION: synthetic

<400> SEQUENCE: 130
```

```
gctgtcaacg atacgctacg taacggcatg acagtgtttt tttttttttt tttttttttt      60
```

<210> SEQ ID NO 131
<211> LENGTH: 29
<212> TYPE: DNA
<213> ORGANISM: Artificial
<220> FEATURE:
<223> OTHER INFORMATION: synthetic

<400> SEQUENCE: 131

```
ctactactac taaaggatcc gtcgacatc                                        29
```

<210> SEQ ID NO 132
<211> LENGTH: 25
<212> TYPE: DNA
<213> ORGANISM: Artificial
<220> FEATURE:
<223> OTHER INFORMATION: synthetic

<400> SEQUENCE: 132

```
gctgtcaacg atacgctacg taacg                                            25
```

<210> SEQ ID NO 133
<211> LENGTH: 23
<212> TYPE: DNA
<213> ORGANISM: Artificial
<220> FEATURE:
<223> OTHER INFORMATION: synthetic

<400> SEQUENCE: 133

```
cgctacgtaa cggcatgaca gtg                                              23
```

<210> SEQ ID NO 134
<211> LENGTH: 23
<212> TYPE: DNA
<213> ORGANISM: Artificial
<220> FEATURE:
<223> OTHER INFORMATION: synthetic

<400> SEQUENCE: 134

```
ttcctgggtg atcaatggcg aga                                              23
```

<210> SEQ ID NO 135
<211> LENGTH: 20
<212> TYPE: DNA
<213> ORGANISM: Artificial
<220> FEATURE:
<223> OTHER INFORMATION: synthetic

<400> SEQUENCE: 135

```
tccccgggcg attcctgtct                                                  20
```

<210> SEQ ID NO 136
<211> LENGTH: 26
<212> TYPE: DNA
<213> ORGANISM: Artificial
<220> FEATURE:
<223> OTHER INFORMATION: synthetic

<400> SEQUENCE: 136

```
tccatcacat caccctcctc cttcaa                                           26
```

<210> SEQ ID NO 137
<211> LENGTH: 19
<212> TYPE: DNA

```
<213> ORGANISM: Artificial
<220> FEATURE:
<223> OTHER INFORMATION: synthetic

<400> SEQUENCE: 137
gctcccgctg cgtttgtcc                                                    19

<210> SEQ ID NO 138
<211> LENGTH: 24
<212> TYPE: DNA
<213> ORGANISM: Artificial
<220> FEATURE:
<223> OTHER INFORMATION: synthetic

<400> SEQUENCE: 138
caacagacca ccccacaggc tcag                                              24

<210> SEQ ID NO 139
<211> LENGTH: 25
<212> TYPE: DNA
<213> ORGANISM: Artificial
<220> FEATURE:
<223> OTHER INFORMATION: synthetic

<400> SEQUENCE: 139
caaccgttgg ggattacaaa ataga                                             25

<210> SEQ ID NO 140
<211> LENGTH: 19
<212> TYPE: DNA
<213> ORGANISM: Artificial
<220> FEATURE:
<223> OTHER INFORMATION: synthetic

<400> SEQUENCE: 140
ggctgcccag ggagttgct                                                    19

<210> SEQ ID NO 141
<211> LENGTH: 23
<212> TYPE: DNA
<213> ORGANISM: Artificial
<220> FEATURE:
<223> OTHER INFORMATION: synthetic

<400> SEQUENCE: 141
gcagaagctc ccagccagat ctt                                               23

<210> SEQ ID NO 142
<211> LENGTH: 25
<212> TYPE: DNA
<213> ORGANISM: Artificial
<220> FEATURE:
<223> OTHER INFORMATION: synthetic

<400> SEQUENCE: 142
ctagggttcg ctgtcctcac actgc                                             25

<210> SEQ ID NO 143
<211> LENGTH: 19
<212> TYPE: DNA
<213> ORGANISM: Artificial
<220> FEATURE:
<223> OTHER INFORMATION: synthetic

<400> SEQUENCE: 143
gctcccgctg cgtttgtcc                                                    19
```

<210> SEQ ID NO 144
<211> LENGTH: 24
<212> TYPE: DNA
<213> ORGANISM: Artificial
<220> FEATURE:
<223> OTHER INFORMATION: synthetic

<400> SEQUENCE: 144
caacagacca ccccacaggc tcag                                            24

<210> SEQ ID NO 145
<211> LENGTH: 50
<212> TYPE: DNA
<213> ORGANISM: Artificial
<220> FEATURE:
<223> OTHER INFORMATION: synthetic

<400> SEQUENCE: 145
gtcgtatcca gtgcagggtc cgaggtattc gcactggata cgacacactc                50

<210> SEQ ID NO 146
<211> LENGTH: 50
<212> TYPE: DNA
<213> ORGANISM: Artificial
<220> FEATURE:
<223> OTHER INFORMATION: synthetic

<400> SEQUENCE: 146
gtcgtatcca gtgcagggtc cgaggtattc gcactggata cgacagtgcc                50

<210> SEQ ID NO 147
<211> LENGTH: 50
<212> TYPE: DNA
<213> ORGANISM: Artificial
<220> FEATURE:
<223> OTHER INFORMATION: synthetic

<400> SEQUENCE: 147
gtcgtatcca gtgcagggtc cgaggtattc gcactggata cgacacgctc                50

<210> SEQ ID NO 148
<211> LENGTH: 50
<212> TYPE: DNA
<213> ORGANISM: Artificial
<220> FEATURE:
<223> OTHER INFORMATION: synthetic

<400> SEQUENCE: 148
gtcgtatcca gtgcagggtc cgaggtattc gcactggata cgacacaccc                50

<210> SEQ ID NO 149
<211> LENGTH: 50
<212> TYPE: DNA
<213> ORGANISM: Artificial
<220> FEATURE:
<223> OTHER INFORMATION: synthetic

<400> SEQUENCE: 149
gtcgtatcca gtgcagggtc cgaggtattc gcactggata cgacgaaagt                50

<210> SEQ ID NO 150
<211> LENGTH: 50
<212> TYPE: DNA
<213> ORGANISM: Artificial
<220> FEATURE:

<223> OTHER INFORMATION: synthetic

<400> SEQUENCE: 150
gtcgtatcca gtgcagggtc cgaggtattc gcactggata cgacacactc    50

<210> SEQ ID NO 151
<211> LENGTH: 50
<212> TYPE: DNA
<213> ORGANISM: Artificial
<220> FEATURE:
<223> OTHER INFORMATION: synthetic

<400> SEQUENCE: 151
gtcgtatcca gtgcagggtc cgaggtattc gcactggata cgacaccctc    50

<210> SEQ ID NO 152
<211> LENGTH: 50
<212> TYPE: DNA
<213> ORGANISM: Artificial
<220> FEATURE:
<223> OTHER INFORMATION: synthetic

<400> SEQUENCE: 152
gtcgtatcca gtgcagggtc cgaggtattc gcactggata cgaccagaaa    50

<210> SEQ ID NO 153
<211> LENGTH: 24
<212> TYPE: DNA
<213> ORGANISM: Artificial
<220> FEATURE:
<223> OTHER INFORMATION: synthetic

<400> SEQUENCE: 153
accgctaagt gccgccatct tttg    24

<210> SEQ ID NO 154
<211> LENGTH: 21
<212> TYPE: DNA
<213> ORGANISM: Artificial
<220> FEATURE:
<223> OTHER INFORMATION: synthetic

<400> SEQUENCE: 154
gccgccactc aaactgtggg g    21

<210> SEQ ID NO 155
<211> LENGTH: 24
<212> TYPE: DNA
<213> ORGANISM: Artificial
<220> FEATURE:
<223> OTHER INFORMATION: synthetic

<400> SEQUENCE: 155
ggtcataaag tgctgcgaca tttg    24

<210> SEQ ID NO 156
<211> LENGTH: 23
<212> TYPE: DNA
<213> ORGANISM: Artificial
<220> FEATURE:
<223> OTHER INFORMATION: synthetic

<400> SEQUENCE: 156
ttcatgaagt gcttcgattt tgg    23

```
<210> SEQ ID NO 157
<211> LENGTH: 24
<212> TYPE: DNA
<213> ORGANISM: Artificial
<220> FEATURE:
<223> OTHER INFORMATION: synthetic

<400> SEQUENCE: 157
agtctacact cagccttgag ggca                                            24

<210> SEQ ID NO 158
<211> LENGTH: 22
<212> TYPE: DNA
<213> ORGANISM: Artificial
<220> FEATURE:
<223> OTHER INFORMATION: synthetic

<400> SEQUENCE: 158
cggcggatcg tgcatccctt ta                                              22

<210> SEQ ID NO 159
<211> LENGTH: 23
<212> TYPE: DNA
<213> ORGANISM: Artificial
<220> FEATURE:
<223> OTHER INFORMATION: synthetic

<400> SEQUENCE: 159
ccggctaaag tgcatccttt tag                                             23

<210> SEQ ID NO 160
<211> LENGTH: 23
<212> TYPE: DNA
<213> ORGANISM: Artificial
<220> FEATURE:
<223> OTHER INFORMATION: synthetic

<400> SEQUENCE: 160
gccgccaaag tgcttccttt tag                                             23

<210> SEQ ID NO 161
<211> LENGTH: 22
<212> TYPE: DNA
<213> ORGANISM: Artificial
<220> FEATURE:
<223> OTHER INFORMATION: synthetic

<400> SEQUENCE: 161
accgctctct agagggaagc ac                                              22

<210> SEQ ID NO 162
<211> LENGTH: 16
<212> TYPE: DNA
<213> ORGANISM: Artificial
<220> FEATURE:
<223> OTHER INFORMATION: synthetic

<400> SEQUENCE: 162
gtgcagggtc cgaggt                                                     16
```